US009200082B2

(12) United States Patent
Collier et al.

(10) Patent No.: US 9,200,082 B2
(45) Date of Patent: Dec. 1, 2015

(54) METHODS AND COMPOSITIONS INVOLVING FIBRILLIZING POLYPEPTIDES FOR NANOFIBERS

(71) Applicant: The University of Chicago, Chicago, IL (US)

(72) Inventors: Joel Collier, Western Springs, IL (US); Gregory Hudalla, Chicago, IL (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 14/209,757

(22) Filed: Mar. 13, 2014

(65) Prior Publication Data

US 2014/0273148 A1 Sep. 18, 2014

Related U.S. Application Data

(60) Provisional application No. 61/782,193, filed on Mar. 14, 2013.

(51) Int. Cl.
*A61K 47/22* (2006.01)
*C07K 17/06* (2006.01)
*C07K 14/78* (2006.01)

(52) U.S. Cl.
CPC .............. *C07K 17/06* (2013.01); *C07K 14/78* (2013.01)

(58) Field of Classification Search
None
See application file for complete search history.

(56) References Cited

U.S. PATENT DOCUMENTS 8,063,014 B2 * 11/2011 Stupp et al. .................. 514/17.7
2011/0236429 A1 * 9/2011 Hancock et al. ............ 424/278.1

FOREIGN PATENT DOCUMENTS

WO   WO 2008/124646   10/2008
WO   WO 2011/063264 A1 * 5/2011 ............. A61K 47/22

OTHER PUBLICATIONS

Bothner et al (2003) JACS 125: 3200-3201.*
Baldwin, et al., *J Am Chem Soc*. 128:2162, 2006.
Baxa, et al., *PNAS USA*. 99:5253, 2002.
Black, et al., *Adv Mater*. 24:3845, 2012.
Bothner, et al., *J Am Chem Soc*. 125:3200, 2003.
Brodin, et al., *Nat Chem*. 4:375, 2012.
Cardinale, et al., *Trends Biotechnol*. 30:369, 2012.
Collier & Messersmith, *Bioconjug Chem*. 14:748, 2003.
Collier & Segura, *Biomaterials*. 32:4198, 2011.
Collier, et al., *Chem Sox Rev*. 39:3413, 2010.
Collier, *Soft Matter*. 4:2310, 2008.
Gasiorowski & Collier, *Biomacromolecules*. 12:3549, 2011.
Guglielmi, et al., *Biomaterials*. 30:829, 2009.
Guler, et al., *Bioconjug Chem*. 16:501, 2005.
Horii, et al., *PLoS One*. 2:e190, 2007.
Hudalla & Murphy, *Adv Funct Mater*. 21(10):1754-1768, 2011.
Hudalla, et al., *Adv Healthc Mater*. 2(8):1114-9, 2013.
Hudalla, Presentation on Beta Tails from NJ Biomaterials, Presentation Mar. 14, 2012.
Jung, et al., *Integr Biol (Camb)*. 3:185, 2011.
Kim, et al., *ACS Chem Biol*. 1:461, 2006.
King, et al., *Science*. 336:1171, 2012.
Kolattukudy, et al., *Meth Enzymol*. 71:652, 1981.
Leng, et al., *Angewandte Chemie Intl Ed*. 49:7243, 2010.
Lim, et al., *Chem Soc Rev*. 38:925, 2009.
Malyala & Singh, *J Pharm Sci*. 97:2041, 2008.
Marini, et al., *Nano Lett*. 2:295, 2002.
Matson & Stupp, *Chem Commun (Camb)*. 48:26, 2012.
Matson, et al., *Chem Commun (Camb)*. 47:7962, 2011.
Men, et al., *Nano Lett*. 9:2246, 2009.
Minten, et al., *Chem Sci*. 2:358, 2011.
Minten, et al., *J Am Chem Soc*. 131:17771, 2009.
Pagel, et al., *Chem Biochem*. 9:531, 2008.
Pagel, et al., *J. Am. Chem. Soc*. 128: 2196, 2006.
Patterson, et al., *ACS Nano*. 6:5000, 2012.
Rudra, et al., *PNAS USA*. 107:622, 2010.
Sangiambut, et al., *Adv Mater*. Doi: 10.1002/adma.201204127, 2013.
Sinclair, et al., *Nat Nanotechnol*. 6:558, 2011.
Sinthuvanich, et al., *J Am Chem Soc*. 134:6210, 2012.
Takahashi, et al., *Chem Biochem*. 3:637, 2002.
Veiga, et al., *Biomaterials*. 33:8907, 2012.
Wahome, et al., *Chem Biol Drug Des*. 80:349, 2012.
Wang, et al., *J Am Soc Nephrol*. 22:704, 2011.
Webber, et al., *Biomaterials*. 33:6823, 2012.
Wheeldon, et al., *J Mol Biol*. 392:129, 2009.
Wheeldon, et al., *PNAS USA*. 105:15275, 2008.
Woolfson & Mahmoud, *Chem Soc Rev*. 39:3464, 2010.
Zhang, et al., *Biomaterials*. 16:1385, 1995.

* cited by examiner

*Primary Examiner* — Karlheinz R Skowronek
*Assistant Examiner* — Mindy Newman
(74) *Attorney, Agent, or Firm* — Norton Rose Fulbright US LLP

(57) ABSTRACT

Embodiments of the invention are directed to fibrillar adjuvants. For example, epitopes assembled by a synthetic peptide domain into nanofibers comprising a β-fibrillization peptide may elicit high antibody titers in the absence of any adjuvant. In certain embodiments, multiple different antigens may be integrated into polypeptide nanofibers, providing biomaterials with modular and precise composition of bioactive proteins.

20 Claims, 10 Drawing Sheets

SEQUENCE LISTING

```
<160> NUMBER OF SEQ ID NOS: 73

<210> SEQ ID NO 1
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 1

Leu Val Val Leu His Ser Glu Leu His Lys Leu Lys Ser Glu Leu
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 2

Leu Val Val Leu His Ser His Leu Glu Lys Leu Lys Ser Glu Leu
1               5                   10                  15

<210> SEQ ID NO 3
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 3

Leu Lys Val Glu Leu Glu Lys Leu Lys Ser Glu Leu Val Val Leu His
1               5                   10                  15

Ser Glu Leu His Lys Leu Lys Ser Glu Leu
            20                  25

<210> SEQ ID NO 4
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 4

Leu Lys Val Glu Leu Glu Lys Leu Lys Ser Glu Leu Val Val Leu His
1               5                   10                  15

Ser His Leu Glu Lys Leu Lys Ser Glu Leu
            20                  25

<210> SEQ ID NO 5
<211> LENGTH: 26
<212> TYPE: PRT
<213> ORGANISM: Artificial Sequence
<220> FEATURE:
<223> OTHER INFORMATION: Synthetic Peptide
```

```
-continued

<400> SEQUENCE: 5

Leu Lys Val Glu Leu Lys Glu Leu Lys Lys Glu Leu Val Val Leu Lys
1               5                   10                  15

Ser Glu Leu Lys Glu Leu Lys Lys Glu Leu
            20                  25

<210> SEQ ID NO 6
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 6

Gln Gln Lys Phe Gln Phe Gln Phe Glu Gln Gln
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 7

Gln Gln Lys Phe Gln Phe Gln Phe His Gln Gln
1               5                   10

<210> SEQ ID NO 8
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 8

Phe Lys Phe Glu Phe Lys Phe Glu
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 9

Lys Phe Gln Phe Gln Phe Glu
1               5

<210> SEQ ID NO 10
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 10

Gln Gln Arg Phe Gln Phe Gln Phe Glu Gln Gln
1               5                   10

<210> SEQ ID NO 11
<211> LENGTH: 11
<212> TYPE: PRT
<213> ORGANISM: Artificial Sequence
<220> FEATURE:
```

-continued

<223> OTHER INFORMATION: Synthetic Peptide

<400> SEQUENCE: 11

Gln Gln Arg Phe Gln Trp Gln Phe Glu Gln Gln
1               5                   10

<210> SEQ ID NO 12
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 12

Phe Glu Phe Glu Phe Lys Phe Lys Phe Glu Phe Glu Phe Lys Phe Lys
1               5                   10                  15

<210> SEQ ID NO 13
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 13

Gln Gln Arg Phe Glu Trp Glu Phe Glu Gln Gln
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(11)
<223> OTHER INFORMATION: X denotes ornithine

<400> SEQUENCE: 14

Gln Gln Xaa Phe Xaa Trp Xaa Phe Gln Gln Gln
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 15

Phe Lys Phe Glu Phe Lys Phe Glu Phe Lys Phe Glu
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 16

Phe Lys Phe Gln Phe Lys Phe Gln Phe Lys Phe Gln
1               5                   10

<210> SEQ ID NO 17
<211> LENGTH: 16

```
<212> TYPE: PRT
<213> ORGANISM: Artificial Sequence
<220> FEATURE:
<223> OTHER INFORMATION: Synthetic Peptide

<400> SEQUENCE: 17

Ala Glu Ala Lys Ala Glu Ala Lys Ala Glu Ala Lys Ala Glu Ala Lys
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 18

Ala Glu Ala Glu Ala Lys Ala Lys Ala Glu Ala Glu Ala Lys Ala Lys
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 19

Ala Glu Ala Glu Ala Glu Ala Glu Ala Lys Ala Lys Ala Lys Ala Lys
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 20

Arg Ala Asp Ala Arg Ala Asp Ala Arg Ala Asp Ala Arg Ala Asp Ala
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 21

Arg Ala Arg Ala Asp Ala Asp Ala Arg Ala Arg Ala Asp Ala Asp Ala
1               5                   10                  15

<210> SEQ ID NO 22
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 22

Ser Gly Arg Gly Tyr Asx Leu Gly Gly Gln Gly Ala Gly Ala Ala Ala
1               5                   10                  15

Ala Ala Gly Gly Ala Gly Gln Gly Gly Tyr Gly Gly Leu Gly Ser Gln
                20                  25                  30

Gly
```

```
<210> SEQ ID NO 23
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: X = V, A, S, or P

<400> SEQUENCE: 23

Glu Trp Glu Xaa Glu Xaa Glu Xaa Glu Xaa
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: X = V, A, S, or P

<400> SEQUENCE: 24

Trp Lys Xaa Lys Xaa Lys Xaa Lys Xaa Lys
1               5                   10

<210> SEQ ID NO 25
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 25

Lys Trp Lys Val Lys Val Lys Val Lys Val Lys Val Lys Val Lys
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 26

Leu Leu Leu Leu Lys Lys Lys Lys Lys Lys Lys Lys Leu Leu Leu Leu
1               5                   10                  15

<210> SEQ ID NO 27
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 27

Val Lys Val Lys Val Lys Val Lys Val Asp Pro Pro Thr Lys Val Lys
1               5                   10                  15

Val Lys Val Lys Val
                20

<210> SEQ ID NO 28
```

<211> LENGTH: 21
<212> TYPE: PRT
<213> ORGANISM: Artificial Sequence
<220> FEATURE:
<223> OTHER INFORMATION: Synthetic Peptide

<400> SEQUENCE: 28

Val Lys Val Lys Val Lys Val Lys Val Asp Pro Pro Thr Lys Val Lys
1               5                   10                  15

Thr Lys Val Lys Val
            20

<210> SEQ ID NO 29
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 29

Lys Val Lys Val Lys Val Lys Val Lys Asp Pro Pro Ser Val Lys Val
1               5                   10                  15

Lys Val Lys Val Lys
            20

<210> SEQ ID NO 30
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 30

Val Lys Val Lys Val Lys Val Lys Val Asp Pro Pro Ser Lys Val Lys
1               5                   10                  15

Val Lys Val Lys Val
            20

<210> SEQ ID NO 31
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 31

Val Lys Val Lys Val Lys Thr Lys Val Asp Pro Pro Thr Lys Val Lys
1               5                   10                  15

Thr Lys Val Lys Val
            20

<210> SEQ ID NO 32
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 32

Lys Lys Ser Leu Ser Leu Ser Leu Ser Leu Ser Leu Ser Leu Lys Lys
1               5                   10                  15

<210> SEQ ID NO 33
<211> LENGTH: 10
<212> TYPE: PRT

```
<213> ORGANISM: Artificial Sequence
<220> FEATURE:
<223> OTHER INFORMATION: Synthetic Peptide

<400> SEQUENCE: 33

Tyr Thr Ile Ala Ala Leu Leu Ser Pro Tyr
1               5                   10

<210> SEQ ID NO 34
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 34

Leu Glu Lys Leu Lys Ser Glu
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 35

Leu Val Val Leu His Ser Glu
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 36

Leu His Lys Leu Lys Ser Glu
1               5

<210> SEQ ID NO 37
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 37

Arg Ala Asp Ala Arg Gly Asp Ala Arg Ala Asp Ala Arg Gly Asp Ala
1               5                   10                  15

<210> SEQ ID NO 38
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 38

Arg Ala Asp Ala Arg Ala Asp Ala
1               5

<210> SEQ ID NO 39
<211> LENGTH: 8
<212> TYPE: PRT
<213> ORGANISM: Artificial Sequence
```

```
<220> FEATURE:
<223> OTHER INFORMATION: Synthetic Peptide

<400> SEQUENCE: 39

Arg Ala Arg Ala Asp Ala Asp Ala
1               5

<210> SEQ ID NO 40
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 40

Ala Glu Ala Lys Ala Glu Ala Lys
1               5

<210> SEQ ID NO 41
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 41

Arg Ala Glu Ala Arg Ala Glu Ala Arg Ala Glu Ala Arg Ala Glu Ala
1               5                   10                  15

<210> SEQ ID NO 42
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 42

Arg Ala Glu Ala Arg Ala Glu Ala
1               5

<210> SEQ ID NO 43
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 43

Lys Ala Asp Ala Lys Ala Asp Ala Lys Ala Asp Ala Lys Ala Asp Ala
1               5                   10                  15

<210> SEQ ID NO 44
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 44

Lys Ala Asp Ala Lys Ala Asp Ala
1               5

<210> SEQ ID NO 45
<211> LENGTH: 17
<212> TYPE: PRT
<213> ORGANISM: Artificial Sequence
<220> FEATURE:
```

<223> OTHER INFORMATION: Synthetic Peptide

<400> SEQUENCE: 45

Ala Glu Ala Glu Ala His Ala His Ala Glu Ala Glu Ala His Ala His
1               5                   10                  15
Ala

<210> SEQ ID NO 46
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 46

Ala Glu Ala Glu Ala His Ala His Ala
1               5

<210> SEQ ID NO 47
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 47

Phe Glu Phe Lys Phe Glu Phe Lys
1               5

<210> SEQ ID NO 48
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 48

Leu Glu Leu Glu Leu Lys Leu Lys Leu Glu Leu Glu Leu Lys Leu Lys
1               5                   10                  15

<210> SEQ ID NO 49
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 49

Leu Glu Leu Glu Leu Lys Leu Lys
1               5

<210> SEQ ID NO 50
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 50

Ala Glu Ala Glu Ala Glu Ala Glu Ala Lys Ala Lys
1               5                   10

<210> SEQ ID NO 51
<211> LENGTH: 8
<212> TYPE: PRT
<213> ORGANISM: Artificial Sequence

```
<220> FEATURE:
<223> OTHER INFORMATION: Synthetic Peptide

<400> SEQUENCE: 51

Ala Glu Ala Glu Ala Lys Ala Lys
1               5

<210> SEQ ID NO 52
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 52

Lys Ala Lys Ala Lys Ala Lys Ala Glu Ala Glu Ala Glu Ala Glu Ala
1               5                   10                  15

<210> SEQ ID NO 53
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 53

Arg Ala Arg Ala Arg Ala Arg Ala Asp Ala Asp Ala Asp Ala Asp Ala
1               5                   10                  15

<210> SEQ ID NO 54
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 54

Ala Asp Ala Asp Ala Asp Ala Asp Ala Arg Ala Arg Ala Arg Ala Arg
1               5                   10                  15

<210> SEQ ID NO 55
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 55

Asp Ala Asp Ala Asp Ala Asp Ala Arg Ala Arg Ala Arg Ala Arg Ala
1               5                   10                  15

<210> SEQ ID NO 56
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 56

Ala Asp Ala Asp Ala Asp Ala Asp Ala Arg Ala Arg Ala Arg Ala Arg
1               5                   10                  15

<210> SEQ ID NO 57
<211> LENGTH: 16
<212> TYPE: PRT
<213> ORGANISM: Artificial Sequence
<220> FEATURE:
```

<223> OTHER INFORMATION: Synthetic Peptide

<400> SEQUENCE: 57

His Glu His Glu His Lys His Lys His Glu His Glu His Lys His Lys
1               5                   10                  15

<210> SEQ ID NO 58
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 58

His Glu His Glu His Lys His Lys
1               5

<210> SEQ ID NO 59
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 59

Val Glu Val Glu Val Glu Val Glu Val Glu Val Glu Val Glu Val Glu
1               5                   10                  15

Val Glu Val Glu
            20

<210> SEQ ID NO 60
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 60

Arg Phe Arg Phe Arg Phe Arg Phe Arg Phe Arg Phe Arg Phe Arg Phe
1               5                   10                  15

Arg Phe Arg Phe
            20

<210> SEQ ID NO 61
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 61

Met Ala Leu Lys Val Glu Leu Glu Lys Leu Lys Ser Glu Leu Val Val
1               5                   10                  15

Leu His Ser Glu Leu His Lys Leu Lys Ser Glu Leu
            20                  25

<210> SEQ ID NO 62
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 62

Trp Gly Ser Gly Ser Met Ala Leu Lys Val Glu Leu Glu Lys Leu Lys

```
                1               5                  10                  15
        Ser Glu Leu Val Val Leu His Ser Glu Leu His Lys Leu Lys Ser Glu
                        20                  25                  30

Leu

<210> SEQ ID NO 63
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 63

Gly Lys Pro Glu Gly Glu Lys Pro Lys Ser Glu Gly Gly Pro Gly His
1               5                   10                  15

Ser Glu Gly His Lys Pro Lys Ser Glu Gly
            20                  25

<210> SEQ ID NO 64
<211> LENGTH: 927
<212> TYPE: DNA
<213> ORGANISM: Artificial Sequence
<220> FEATURE:
<223> OTHER INFORMATION: Synthetic Primer

<400> SEQUENCE: 64
atggccctga aagtggaact ggaaaaactg aaaagcgaac tggtggtgct gcatagcgaa      60
ctgcataaac tgaaaagcga actgggatcc ggcggtggcg gttctggtgg cggtggctct    120
ggcggtggcg gcggtggagg atccggcggt ggcggttctg gtggcggtgg ctctggcggt    180
ggcggttcta gtaaaggaga gaacttttc actggagttg tcccaattct tgttgaatta    240
gatggtgatg ttaatgggca aaattttct gtcagtggag agggtgaagg tgatgcaaca    300
tacggaaaac ttacccttaa atttatttgc actactggaa aactacctgt tccatggcca    360
acacttgtca ctactttctc ttatggtgtt caatgctttt cccgttatcc ggatcatatg    420
aaacggcatg actttttcaa gagtgccatg cccgaaggtt atgtacagga acgcactata    480
tctttcaaag atgacgggaa ctacaagacg cgtgctgaag tcaagtttga aggtgatacc    540
cttgttaatc gtatcgagtt aaaaggtatt gattttaaag aagatggaaa cattctcgga    600
cacaaactcg agtacaacta taactcacac aatgtataca tcacggcaga caacaaaag    660 aatggaatca aagctaactt caaaattcgc cacaacattg aagatggatc cgttcaacta    720
gcagaccatt atcaacaaaa tactccaatt ggcgatggcc ctgtcctttt accagacaac    780
cattacctgt cgacacaatc tgccctttcg aaagatccca acgaaaagcg tgaccacatg    840
gtccttcttg agtttgtaac tgctgctggg attacacatg gcatggatga gctctacaaa    900
ctcgagcacc accaccacca ccactga                                        927

<210> SEQ ID NO 65
<211> LENGTH: 308
<212> TYPE: PRT
<213> ORGANISM: Artificial Sequence
<220> FEATURE:
<223> OTHER INFORMATION: Synthetic Peptide

<400> SEQUENCE: 65

Met Ala Leu Lys Val Glu Leu Glu Lys Leu Lys Ser Glu Leu Val Val
1               5                   10                  15

Leu His Ser Glu Leu His Lys Leu Lys Ser Glu Leu Gly Ser Gly Gly
```

| | | | | | | | 20 | | | | 25 | | | | 30 | | |
|---|---|---|---|---|---|---|---|---|---|---|---|---|---|---|---|---|---|
Gly Gly Ser Gly Gly Gly Ser Gly Gly Gly Gly Gly Gly Ser
 35                  40                  45
Gly Gly Gly Gly Ser Gly Gly Gly Ser Gly Gly Gly Ser Ser
 50                  55                  60
Lys Gly Glu Glu Leu Phe Thr Gly Val Val Pro Ile Leu Val Glu Leu
 65                  70                  75                  80
Asp Gly Asp Val Asn Gly His Lys Phe Ser Val Ser Gly Glu Gly Glu
                     85                  90                  95
Gly Asp Ala Thr Tyr Gly Lys Leu Thr Leu Lys Phe Ile Cys Thr Thr
                100                 105                 110
Gly Lys Leu Pro Val Pro Trp Pro Thr Leu Val Thr Thr Phe Ser Tyr
                115                 120                 125
Gly Val Gln Cys Phe Ser Arg Tyr Pro Asp His Met Lys Arg His Asp
                130                 135                 140
Phe Phe Lys Ser Ala Met Pro Glu Gly Tyr Val Gln Glu Arg Thr Ile
145                 150                 155                 160
Ser Phe Lys Asp Asp Gly Asn Tyr Lys Thr Arg Ala Glu Val Lys Phe
                165                 170                 175
Glu Gly Asp Thr Leu Val Asn Arg Ile Glu Leu Lys Gly Ile Asp Phe
                180                 185                 190
Lys Glu Asp Gly Asn Ile Leu Gly His Lys Leu Glu Tyr Asn Tyr Asn
                195                 200                 205
Ser His Asn Val Tyr Ile Thr Ala Asp Lys Gln Lys Asn Gly Ile Lys
                210                 215                 220
Ala Asn Phe Lys Ile Arg His Asn Ile Glu Asp Gly Ser Val Gln Leu
225                 230                 235                 240
Ala Asp His Tyr Gln Gln Asn Thr Pro Ile Gly Asp Gly Pro Val Leu
                245                 250                 255
Leu Pro Asp Asn His Tyr Leu Ser Thr Gln Ser Ala Leu Ser Lys Asp
                260                 265                 270
Pro Asn Glu Lys Arg Asp His Met Val Leu Leu Glu Phe Val Thr Ala
                275                 280                 285
Ala Gly Ile Thr His Gly Met Asp Glu Leu Tyr Lys Leu Glu His His
                290                 295                 300
His His His His
305

<210> SEQ ID NO 66
<211> LENGTH: 927
<212> TYPE: DNA
<213> ORGANISM: Artificial Sequence
<220> FEATURE:
<223> OTHER INFORMATION: Synthetic Primer

<400> SEQUENCE: 66
atggccggaa aaccagaagg agaaaaacca aaatcagaag gaggaccagg acactcagaa      60
ggacacaaac caaaatcaga aggaggatcc ggcggtggcg gttctggtgg cggtggctct     120
ggcggtggcg gcgttggagg atccggcggt ggcggttctg gtggcggtgg ctctggcggt     180
ggcggttcta gtaaaggaga gaactttttc actggagttg tcccaattct tgttgaatta     240
gatggtgatg ttaatgggca caaattttct gtcagtggag agggtgaagg tgatgcaaca     300
tacggaaaac ttaccctttaa atttatttgc actactggaa aactacctgt tccatggcca     360
acacttgtca ctactttctc ttatggtgtt caatgctttt cccgttatcc ggatcatatg     420

```
aaacggcatg actttttcaa gagtgccatg cccgaaggtt atgtacagga acgcactata    480
tctttcaaag atgacgggaa ctacaagacg cgtgctgaag tcaagtttga aggtgatacc    540
cttgttaatc gtatcgagtt aaaaggtatt gatttttaaag aagatggaaa cattctcgga   600
```
(Note: line 600 may read "gattttaaag"; reproducing as shown)
```
cacaaactcg agtacaacta taactcacac aatgtataca tcacggcaga caaacaaaag    660
aatggaatca agctaactt caaaattcgc cacaacattg aagatggatc cgttcaacta     720
gcagaccatt atcaacaaaa tactccaatt ggcgatggcc ctgtcctttt accagacaac    780
cattacctgt cgacacaatc tgcccttttcg aaagatccca acgaaaagcg tgaccacatg   840
gtccttcttg agtttgtaac tgctgctggg attacacatg gcatggatga gctctacaaa   900
ctcgagcacc accaccacca ccactga                                         927
```

<210> SEQ ID NO 67
<211> LENGTH: 308
<212> TYPE: PRT
<213> ORGANISM: Artificial Sequence
<220> FEATURE:
<223> OTHER INFORMATION: Synthetic Peptide

<400> SEQUENCE: 67

```
Met Ala Gly Lys Pro Glu Gly Glu Lys Pro Lys Ser Glu Gly Gly Pro
1               5                   10                  15

Gly His Ser Glu Gly His Lys Pro Lys Ser Glu Gly Gly Ser Gly Gly
            20                  25                  30

Gly Gly Ser Gly Gly Gly Gly Ser Gly Gly Gly Gly Gly Gly Gly Ser
        35                  40                  45

Gly Gly Gly Gly Ser Gly Gly Gly Ser Gly Gly Gly Ser Ser
    50                  55                  60

Lys Gly Glu Glu Leu Phe Thr Gly Val Val Pro Ile Leu Val Glu Leu
65                  70                  75                  80

Asp Gly Asp Val Asn Gly His Lys Phe Ser Val Ser Gly Glu Gly Glu
                85                  90                  95

Gly Asp Ala Thr Tyr Gly Lys Leu Thr Leu Lys Phe Ile Cys Thr Thr
            100                 105                 110

Gly Lys Leu Pro Val Pro Trp Pro Thr Leu Val Thr Thr Phe Ser Tyr
        115                 120                 125

Gly Val Gln Cys Phe Ser Arg Tyr Pro Asp His Met Lys Arg His Asp
    130                 135                 140

Phe Phe Lys Ser Ala Met Pro Glu Gly Tyr Val Gln Glu Arg Thr Ile
145                 150                 155                 160

Ser Phe Lys Asp Asp Gly Asn Tyr Lys Thr Arg Ala Glu Val Lys Phe
                165                 170                 175

Glu Gly Asp Thr Leu Val Asn Arg Ile Glu Leu Lys Gly Ile Asp Phe
            180                 185                 190

Lys Glu Asp Gly Asn Ile Leu Gly His Lys Leu Glu Tyr Asn Tyr Asn
        195                 200                 205

Ser His Asn Val Tyr Ile Thr Ala Asp Lys Gln Lys Asn Gly Ile Lys
    210                 215                 220

Ala Asn Phe Lys Ile Arg His Asn Ile Glu Asp Gly Ser Val Gln Leu
225                 230                 235                 240

Ala Asp His Tyr Gln Gln Asn Thr Pro Ile Gly Asp Gly Pro Val Leu
                245                 250                 255

Leu Pro Asp Asn His Tyr Leu Ser Thr Gln Ser Ala Leu Ser Lys Asp
            260                 265                 270
```

```
Pro Asn Glu Lys Arg Asp His Met Val Leu Glu Phe Val Thr Ala
        275                 280                 285

Ala Gly Ile Thr His Gly Met Asp Glu Leu Tyr Lys Leu Glu His His
        290                 295                 300

His His His His
305

<210> SEQ ID NO 68
<211> LENGTH: 894
<212> TYPE: DNA
<213> ORGANISM: Artificial Sequence
<220> FEATURE:
<223> OTHER INFORMATION: Synthetic Primer

<400> SEQUENCE: 68
atggccggaa aaccagaagg agaaaaacca aaatcagaag gaggaccagg acactcagaa      60
ggacacaaac caaatcagaa aggaggatcc ggcggtggcg gttctggtgg cggtggctct    120
ggcggtggcg gcggtggagg atccggcggt ggcggttctg gtggcggtgg ctctggcggt    180
ggcggttcta gtgacgacaa caccgaggac gtcatcaagg agttcatgca gttcaaggtg    240
cgcatggagg gctccgtgaa cggccactac ttcgagatcg agggcgaggg cgagggcaag    300
ccctacgagg gcacccagac cgccaagctg caggtgacca agggcggccc cctgcccttc    360
gcctgggaca tcctgtcccc ccagttccag tacggctcca aggcctacgt gaagcacccc    420
gccgacatcc ccgactacat gaagctgtcc ttccccgagg gcttcacctg ggagcgctcc    480
atgaacttcg aggacggcgg cgtggtggag gtgcagcagg actcctccct gcaggacggc    540
accttcatct acaaggtgaa gttcaagggc gtgaacttcc ccgccgacgg ccccgtaatg    600
cagaagaaga ctgccggctg ggagccctcc accgagaagc tgtaccccca ggacggcgtg    660
ctgaagggcg agatctccca cgccctgaag ctgaaggacg gcggccacta cctgcgac     720 ttcaagaccg tgtacaaggc caagaagccc gtgcagctgc ccggcaacca ctacgtggac    780
tccaagctgg acatcaccaa ccacaacgag gactacaccg tggtggagca gtacgagcac    840
gccgaggccc gccactccgg ctcccagctc gagcaccacc accaccacca ctga           894

<210> SEQ ID NO 69
<211> LENGTH: 295
<212> TYPE: PRT
<213> ORGANISM: Artificial Sequence
<220> FEATURE:
<223> OTHER INFORMATION: Synthetic Peptide

<400> SEQUENCE: 69

Met Ala Leu Lys Val Glu Leu Glu Lys Leu Lys Ser Glu Leu Val Val
1               5                   10                  15

Leu His Ser His Leu Glu Lys Leu Lys Ser Glu Leu Gly Ser Gly Gly
                20                  25                  30

Gly Gly Ser Gly Gly Gly Gly Ser Gly Gly Gly Gly Gly Gly Gly Ser
        35                  40                  45

Gly Gly Gly Gly Ser Gly Gly Gly Ser Gly Gly Gly Ser Ser
    50                  55                  60

Asp Asp Asn Thr Glu Asp Val Ile Lys Glu Phe Met Gln Phe Lys Val
65                  70                  75                  80

Arg Met Glu Gly Ser Val Asn Gly His Tyr Phe Glu Ile Glu Gly Glu
                85                  90                  95

Gly Glu Gly Lys Pro Tyr Glu Gly Thr Gln Thr Ala Lys Leu Gln Val
```

|     |     |     | 100 |     |     |     | 105 |     |     |     | 110 |     |
| --- | --- | --- | --- | --- | --- | --- | --- | --- | --- | --- | --- | --- |
| Thr | Lys | Gly | Gly | Pro | Leu | Pro | Phe | Ala | Trp | Asp | Ile | Leu | Ser | Pro | Gln |
|     |     |     |     | 115 |     |     |     |     | 120 |     |     |     |     | 125 |     |

Phe Gln Tyr Gly Ser Lys Ala Tyr Val Lys His Pro Ala Asp Ile Pro
    130                 135                 140

Asp Tyr Met Lys Leu Ser Phe Pro Glu Gly Phe Thr Trp Glu Arg Ser
145                 150                 155                 160

Met Asn Phe Glu Asp Gly Gly Val Val Glu Val Gln Gln Asp Ser Ser
                165                 170                 175

Leu Gln Asp Gly Thr Phe Ile Tyr Lys Val Lys Phe Lys Gly Val Asn
            180                 185                 190

Phe Pro Ala Asp Gly Pro Val Met Gln Lys Lys Thr Ala Gly Trp Glu
        195                 200                 205

Pro Ser Thr Glu Lys Leu Tyr Pro Gln Asp Gly Val Leu Lys Gly Glu
    210                 215                 220

Ile Ser His Ala Leu Lys Leu Lys Asp Gly Gly His Tyr Thr Cys Asp
225                 230                 235                 240

Phe Lys Thr Val Tyr Lys Ala Lys Lys Pro Val Gln Leu Pro Gly Asn
                245                 250                 255

His Tyr Val Asp Ser Lys Leu Asp Ile Thr Asn His Asn Glu Asp Tyr
            260                 265                 270

Thr Val Val Glu Gln Tyr Glu His Ala Glu Ala Arg His Ser Gly Ser
        275                 280                 285

Gln His His His His His His
    290                 295

<210> SEQ ID NO 70
<211> LENGTH: 915
<212> TYPE: DNA
<213> ORGANISM: Artificial Sequence
<220> FEATURE:
<223> OTHER INFORMATION: Synthetic Primer

<400> SEQUENCE: 70

| atggcactga aagtcgaact ggaaaaactg aaatcggaac tggtcgtcct gcactcgcac | 60 |
| ctggaaaaac tgaaatcgga actgggtagc ggtggcggtg gctctggtgg cggtggcagt | 120 |
| ggtggcggtg gcgtggcgg ttccggcggt ggcggttcag gcggtggcgg ttcgggcggt | 180 |
| ggcggtagct ctatggttag caaaggtgaa gaactgttta ccggcgtggt tccgattctg | 240 |
| gtcgaactgg atggtgacgt gaatggccat aaattcagtg tgtccggcga aggtgaaggc | 300 |
| gatgcgacct atggtaaact gacgctgaaa tttatctgca ccacgggtaa actgccggtt | 360 |
| ccgtggccga ccctggtcac cacgctgacg tatggtgtcc agtgtttcag ccgctacccg | 420 |
| gatcatatga acaacacga cttttcaaa tctgcgatgc cggaaggtta tgtgcaggaa | 480 |
| cgtaccattt tctttaaaga tgacggcaac tacaaaaccc gcgccgaagt gaaatttgaa | 540 |
| ggtgatacgc tggttaaccg tattgaactg aaaggcatcg atttcaaaga agacggtaat | 600 |
| atcctgggcc ataaactgga atacaactac aactcacaca acgtctacat tatggcagat | 660 |
| aaacagaaaa acggtatcaa agtgaacttc aaaatccgcc ataatatcga agatggctcc | 720 |
| gttcaactgg ctgaccacta tcagcaaaac accccgattg gtgatggccc ggttctgctg | 780 |
| ccggacaatc attacctgtc aacgcagtcg gcactgagca agatccgaa cgaaaaacgt | 840 |
| gaccacatgg ttctgctgga atttgtcacg gctgcgggta ttacgctggg tatggacgaa | 900 |
| ctgtataaac tcgag | 915 |

<210> SEQ ID NO 71
<211> LENGTH: 309
<212> TYPE: PRT
<213> ORGANISM: Artificial Sequence
<220> FEATURE:
<223> OTHER INFORMATION: Synthetic Peptide

<400> SEQUENCE: 71

Met Ala Leu Lys Val Glu Leu Glu Lys Leu Lys Ser Glu Leu Val Val
1               5                   10                  15

Leu His Ser His Leu Glu Lys Leu Lys Ser Glu Leu Gly Ser Gly Gly
                20                  25                  30

Gly Gly Ser Gly Gly Gly Ser Gly Gly Gly Gly Gly Gly Ser
            35                  40                  45

Gly Gly Gly Gly Ser Gly Gly Ser Gly Gly Gly Ser Ser
            50                  55                  60

Met Val Ser Lys Gly Glu Glu Leu Phe Thr Gly Val Val Pro Ile Leu
65                  70                  75                  80

Val Glu Leu Asp Gly Asp Val Asn Gly His Lys Phe Ser Val Ser Gly
                85                  90                  95

Glu Gly Glu Gly Asp Ala Thr Tyr Gly Lys Leu Thr Leu Lys Phe Ile
                100                 105                 110

Cys Thr Thr Gly Lys Leu Pro Val Pro Trp Pro Thr Leu Val Thr Thr
                115                 120                 125

Leu Thr Tyr Gly Val Gln Cys Phe Ser Arg Tyr Pro Asp His Met Lys
        130                 135                 140

Gln His Asp Phe Phe Lys Ser Ala Met Pro Glu Gly Tyr Val Gln Glu
145                 150                 155                 160

Arg Thr Ile Phe Phe Lys Asp Asp Gly Asn Tyr Lys Thr Arg Ala Glu
                165                 170                 175

Val Lys Phe Glu Gly Asp Thr Leu Val Asn Arg Ile Glu Leu Lys Gly
                180                 185                 190

Ile Asp Phe Lys Glu Asp Gly Asn Ile Leu Gly His Lys Leu Glu Tyr
            195                 200                 205

Asn Tyr Asn Ser His Asn Val Tyr Ile Met Ala Asp Lys Gln Lys Asn
    210                 215                 220

Gly Ile Lys Val Asn Phe Lys Ile Arg His Asn Ile Glu Asp Gly Ser
225                 230                 235                 240

Val Gln Leu Ala Asp His Tyr Gln Gln Asn Thr Pro Ile Gly Asp Gly
                245                 250                 255

Pro Val Leu Leu Pro Asp Asn His Tyr Leu Ser Thr Gln Ser Ala Leu
                260                 265                 270

Ser Lys Asp Pro Asn Glu Lys Arg Asp His Met Val Leu Leu Glu Phe
        275                 280                 285

Val Thr Ala Ala Gly Ile Thr Leu Gly Met Asp Glu Leu Tyr Lys His
        290                 295                 300

His His His His His
305

<210> SEQ ID NO 72
<211> LENGTH: 813
<212> TYPE: DNA
<213> ORGANISM: Artificial Sequence
<220> FEATURE:
<223> OTHER INFORMATION: Synthetic Primer

<400> SEQUENCE: 72

```
atggccctga aagtggaact ggaaaaactg aaaagcgaac tggtggtgct gcatagcgaa      60
ctgcataaac tgaaaagcga actgggatcc ggcggtggcg ttctggtgg cggtggctct     120
ggcggtggcg ttctagatc tggcctgcct acttctaacc ctgcccagga gcttgaggcg     180
cgccagcttg gtagaacaac tcgcgacgat ctgatcaacg gcaatagcgc ttcctgcgcc     240
gatgtcatct tcatttatgc ccgaggttca acagagacgg gcaacttggg taccctcggt     300
cctagcattg cctccaacct tgagtccgcg ttcggcaagg acggtgtctg gattcagggc     360
gttggcggtg cctaccgtgc cactcttgga gacaatgctc tccctcgcgg aacctctagc     420
gccgcaatca gggagatgct cggtctcttc agcaggcca acaccaagtg ccctgacgcg      480
actttgatcg ccggtggcta cagccagggt gctgcacttg cagccgcctc catcgaggac     540
ctcgactcgg ccattcgtga caagatcgcc ggaactgttc tgttcggcta taccaagaac     600
ctacagaacc gtggccgaat ccccaactac cctgccgata ggaccaaggt cttctgcaat     660
acaggggatc tcgtttgtac tggtagcttg atcgttgctg cacctcactt ggcgtatggt     720
cctgatgctc gtggccctgc ccctgagttc ctcatcgaga aggttcgggc tgtccgtggt     780
tctgctctcg agcaccacca ccaccaccac tga                                 813
```

```
<210> SEQ ID NO 73
<211> LENGTH: 270
<212> TYPE: PRT
<213> ORGANISM: Artificial Sequence
<220> FEATURE:
<223> OTHER INFORMATION: Synthetic Peptide
```

<400> SEQUENCE: 73

```
Met Ala Leu Lys Val Glu Leu Glu Lys Leu Lys Ser Glu Leu Val Val
  1               5                  10                  15

Leu His Ser Glu Leu His Lys Leu Lys Ser Glu Leu Gly Ser Gly Gly
                 20                  25                  30

Gly Gly Ser Gly Gly Gly Ser Gly Gly Gly Ser Arg Ser Gly
             35                  40                  45

Leu Pro Thr Ser Asn Pro Ala Gln Glu Leu Glu Ala Arg Gln Leu
         50                  55                  60

Arg Thr Thr Arg Asp Asp Leu Ile Asn Gly Asn Ser Ala Ser Cys Ala
 65                  70                  75                  80

Asp Val Ile Phe Ile Tyr Ala Arg Gly Ser Thr Glu Thr Gly Asn Leu
                 85                  90                  95

Gly Thr Leu Gly Pro Ser Ile Ala Ser Asn Leu Glu Ser Ala Phe Gly
            100                 105                 110

Lys Asp Gly Val Trp Ile Gln Gly Val Gly Gly Ala Tyr Arg Ala Thr
            115                 120                 125

Leu Gly Asp Asn Ala Leu Pro Arg Gly Thr Ser Ser Ala Ala Ile Arg
        130                 135                 140

Glu Met Leu Gly Leu Phe Gln Gln Ala Asn Thr Lys Cys Pro Asp Ala
145                 150                 155                 160

Thr Leu Ile Ala Gly Gly Tyr Ser Gln Gly Ala Ala Leu Ala Ala Ala
                165                 170                 175

Ser Ile Glu Asp Leu Asp Ser Ala Ile Arg Asp Lys Ile Ala Gly Thr
            180                 185                 190

Val Leu Phe Gly Tyr Thr Lys Asn Leu Gln Asn Arg Gly Arg Ile Pro
        195                 200                 205
```

-continued

```
Asn Tyr Pro Ala Asp Arg Thr Lys Val Phe Cys Asn Thr Gly Asp Leu
    210                 215                 220

Val Cys Thr Gly Ser Leu Ile Val Ala Ala Pro His Leu Ala Tyr Gly
225                 230                 235                 240

Pro Asp Ala Arg Gly Pro Ala Pro Glu Phe Leu Ile Glu Lys Val Arg
                245                 250                 255

Ala Val Arg Gly Ser Ala Leu Glu His His His His His
                260                 265                 270
```

METHODS AND COMPOSITIONS INVOLVING FIBRILLIZING POLYPEPTIDES FOR NANOFIBERS

The invention was made with government support under Grant Nos. R01 EB009701 and 1R21AI094444 awarded by the National Institutes of Health. The government has certain rights in the invention. This application claims priority to U.S. Provisional Application Ser. No. 61/782,193 filed on Mar. 14, 2013, which is hereby incorporated herein by reference in its entirety.

BACKGROUND OF THE INVENTION

1. Field of the Invention

Embodiments of this invention are directed generally to biology, medicine, and immunology. Certain aspects are directed to immunogenic fibrils and their use in inducing an immune response.

2. Description of Related Art

Polypeptides that non-covalently assemble into supramolecular structures, such as nanofibers and nanoparticles, are receiving increased interest as biomaterials for diverse applications, including enzyme catalysis (Wheeldon 2009; Baxa 2002; Patterson 2012; Guglielmi 2009) biosensors (Leng 2010; Men 2009), electronics (Baldwin 2006; Wheeldon 2008), tissue engineering (Wang 2011; Horii 2007), drugs and drug delivery (Webber 2012; Matson 2011; Sinthuvanich 2012), and immunotherapy (Rudra 2010; Hudalla 2013; Black 2012; Wahome 2012). In part, this widespread applicability arises from the ability to incorporate a self-assembling domain and a bioactive ligand, such as a peptide, protein, or nucleic acid, into a single molecule via recombinant genetic fusion or chemical synthesis approaches, without perturbing the assembly or bioactive properties of the respective domains (Cardinale 2012; Lim 2009; Woolfson 2010; Guler 2005). In addition, mixtures of self-assembling polypeptides with or without appended bioactive ligands co-assemble into multi-component biomaterials, in which molecular composition is governed by the molar ratio of polypeptides present during assembly (Collier 2008; Collier 2010; Matson 2012; Minten 2009; Minten 2011). Importantly, this precise and reproducible compositional control enables use of statistical methods to identify ligand formulations that elicit optimal functional responses (Jung 2011), which can be challenging to achieve with co-polymer blends that are subject to compositional drift. However, supramolecular assemblies bearing multiple different folded protein ligands at precise concentrations have not yet been realized, despite existing approaches to create assemblies having tunable concentration of a single protein ligand (Hudalla 2013; Minten 2009; Sangiambut 2013), or bearing two different biologically active proteins (Leng 2010; Men 2009; Minten 2011). A general approach that enables modular and tunable control over integrated protein ligand composition would provide enormous nanofiber design flexibility, ultimately leading to new biomaterials with unique biological or chemical properties for various downstream applications.

SUMMARY OF THE INVENTION

Certain embodiments are directed to a nanofiber composition comprising a β-sheet nanofiber structure. The structure may have a length of at least, at most, or about 1, 2, 3, 4, 5, 6, 7, 8, 9, 10, 100, 200 nm, 0.25, 0.5, 1, 10, 50 to 10, 25, 50, 100 μm, including all values and ranges there between. In certain aspects, the composition has a molecular weight of at least about 1,000, 5,000, 10,000, 100,000 Da to about $1\times10^6$, $1\times10^7$, $7\times10^8$ Da, including all values and ranges there between.

In certain aspects, the β-sheet nanofiber comprises a plurality of a peptide A and a peptide B. The peptide A may be non-β-sheet peptide tags such as a β-sheet fibrillizing tail (a "βTail) exemplified herein. The non-β-sheet peptide may refer to a peptide that forms a structure other than a β-sheet structure when expressed or isolated. The non-β-sheet peptide may be an α-helical peptide or random coil peptide when expressed or isolated. However, the non-β-sheet peptide tags may form a β-sheet structure in the presence of a β-sheet peptide.

In alternative embodiments, the peptide A may be β-sheet peptides (e.g., Q11 peptide) and may be attached to a compound, such as in the form of a fusion protein. A plurality of a peptide A, each is a β-sheet peptide attached to a compound, may form a nanofiber with a plurality of peptide B, which are β-sheet peptides on their own.

In further aspects, the β-sheet nanofiber comprises a peptide B such as a β-sheet peptide. The β-sheet peptide may refer to a peptide that forms a β-sheet structure. The β-sheet peptides may integrate the non-β-sheet peptide tags into a nanofiber structure.

One or more non-β-sheet peptides may be attached as a tag to one or more compounds. It is contemplated that a single tag (such as a single β-tail peptide molecule) may be attached to 1, 2, 3 or more compounds, which may be the same or different with respect to one another. While compositions comprise a plurality of tags, in some embodiments there are same or different tags that are used. Different tags may be attached to the same or to different compounds. Same tags may be attached to the same or to different compounds, for example, each of a subset of the β-tail molecules is attached to a dGFP compound, and each of a subset of the β-tail molecules is attached to a RFP compound, and each of a subset of the β-tail molecules is attached to a dGFP compound. The molar ratio between the non-β-sheet peptide tag and any compound may be 1:1. 1:2, 1:3, 1:4, 1:5, 1:6, 1:7, 1:8, 1:9, 1:10 or lower such as 10:1, 9:1, 8:1, 7:1, 6:1, 5:1, 4:1, 3:1, 2:1 or any intermediate ranges. In certain aspects, the composition or structure may be heterogeneous by comprising at least two, three, four, five, six, seven, nine, ten, or more (or any range derivable therein) different compounds. Different compounds may be attached to the same or to different tags. Same compounds may be attached to the same or to different compounds. Moreover, there may be 1, 2, 3, 4, 5, 6, 7, 8, 9, 10 or more (or any range derivable therein) different tags.

In some embodiments, the non-β-sheet peptides may comprise one or more α-helical motifs such as coiled-coil motifs. The α-helical motifs may have a sequence of a b c d e f g. The sequence motif may be repeated for about two to seven times. The sequence motifs may be repeated with the same generic structure as described below and same or different specific sequences.

In one, two, three, four, five, six, seven or more or all of the sequence motifs, the position a and d may be non-polar amino acids, hydrophobic amino acids, or non-charged amino acids. For example, a and/or d is Ala (A), Leu (L), Ile (I), Val (V), or a conservative derivative thereof. In particular embodiments, a and/or d is Leu (L) in one, two, three, four, five, six, seven or more or all of the sequence motifs.

In one, two, three, four, five, six, seven or more or all of the sequence motifs, the positions e and g may be charged amino acids, such as Lys (K), Arg (R), His (H), Asp (D), Glu (E) or a conservative derivative thereof. For example, e and g may form or not form attractive electrostatic interactions in one, two, three, four, five, six, seven or more or all of the sequence motifs.

In particular embodiments, one or more of b, c, and, f is a hydrophobic amino acid that favors β-sheet formation or increase β-sheet formation propensity in one, two, three, four, five, six, seven or more or all of the sequence motifs. For example, one or more of b, c, and, f in one or more of the α-helical motifs is Val (V), Tyr (Y), Phe (F), Trp (W), Ile (I), or Thr (T) in one, two, three, four, five, six, seven or more or all of the sequence motifs. More particularly, b, c, and f are beta-sheet forming residues such as Val (V) in one, two, three, four, five, six, seven or more or all of the sequence motifs.

In further aspects, the non-β-sheet peptide comprises an amino acid sequence having at least 50, 60, 70, 75, 80, 85, 90, 95, 99, 100% identity (or any intermediate ranges) with the sequence of LVVLHSELHKLKSEL (SEQ ID NO. 1), LVVLHSHLEKLKSEL (SEQ ID NO. 2), LKVELEKLKSELVVLHSELHKLKSEL (SEQ ID NO. 3), LKVELEKLKSELVVLHSHLEKLKSEL (SEQ ID NO. 4), or LKVELKELKKELVVLKSELKELKKEL (SEQ ID NO. 5). In certain aspects, the non-β-sheet peptide is 6, 7, 8, 9, 10, 11, 12, 13, 14, 15 to 15, 20, 25, 30, 35, 40, 50, 60, 70, 80, 90, 100, 200, 300, 400, 500 amino acids in length, including all values and ranges there between.

In certain aspects, one or more of the alpha helical motifs of the non-β-sheet peptide may further comprise at least one, two, three, four, five, six, seven, eight, nine, ten metal binding amino acids or any range derivable therein. Each of the two metal binding amino acids in one or more of the alpha helical motifs or the non-β-sheet peptide may be spaced by at least one, two, three, four, five, six, seven, eight, nine, ten amino acids or any range derivable therein. The spacing amino acids may be any amino acids, hydrophobic, hydrophilic, charged, metal-binding, or not. The non-β-sheet peptide may also not need any metal binding amino acids, such as LKVELKELKKELVVLKSELKELKKEL (SEQ ID NO. 5).

In particular aspects, one or more of the alpha helical motifs of the non-β-sheet peptide further comprise at least two metal binding amino acids spaced by one amino acid. For example, the non-β-sheet peptide may comprise an amino acid sequence having at least or about 50, 60, 70, 75, 80, 85, 90, 95, 99, or 100% identity (or any range derivable therein) with the sequence of LVVLHSHLEKLKSEL (SEQ ID NO. 2) or LKVELEKLKSELVVLHSHLEKLKSEL (SEQ ID NO. 4).

In further aspects, one or more of the alpha helical motifs further comprise at least two metal binding amino acids spaced by three amino acids. For example, the non-β-sheet peptide may comprise an amino acid sequence having at least or about 50, 60, 70, 75, 80, 85, 90, 95, 99, or 100% identity (or any range derivable therein) with the sequence of LVVLHSELHKLKSEL (SEQ ID NO. 1) or LKVELEKLKSELVVLHSELHKLKSEL (SEQ ID NO. 3).

In further aspects, there may be provided a composition comprising a nanofiber comprising peptide A and peptide B. In further aspects, the peptide A may be attached to any compound at a molar ratio of 1:1. 1:2, 1:3, 1:4, 1:5, 1:6, 1:7, 1:8, 1:9, 1:10 or lower such as 10:1, 9:1, 8:1, 7:1, 6:1, 5:1, 4:1, 3:1, 2:1 or any intermediate ranges. The nanofiber may comprise the same compound or two, three, four, five, six or more different compounds.

The peptide A may comprise an amino acid sequence having at least or about 50, 60, 70, 75, 80, 85, 90, 95, 99, or 100% identity (or any range derivable therein) with the sequence of LVVLHSELHKLKSEL (SEQ ID NO. 1), LVVLHSHLEKLKSEL (SEQ ID NO. 2), LKVELEKLKSELVVLHSELHKLKSEL (SEQ ID NO. 3), LKVELEKLKSELVVLHSHLEKLKSEL (SEQ ID NO. 4), or LKVELKELKKELVVLKSELKELKKEL (SEQ ID NO. 5).

The peptide B may comprise an amino acid sequence having at least or about 50, 60, 70, 80, 85, 90, 95, 99, or 100% identity (or any range derivable therein) with the sequence of QQKFQFQFEQQ (SEQ ID NO. 6); QQKFQFQFHQQ (SEQ ID NO. 7); FKFEFKFE (SEQ ID NO. 8); KFQFQFE (SEQ ID NO. 9); QQRFQFQFEQQ (SEQ ID NO. 10); QQRFQWQFEQQ (SEQ ID NO. 11); FEFEFKFKFEFEFKFK (SEQ ID NO. 12); QQRFEWEFEQQ (SEQ ID NO. 13); QQXFXWXFQQQ (Where X denotes ornithine) (SEQ ID NO. 14); FKFEFKFEFKFE (SEQ ID NO. 15); FKFQFKFQFKFQ (SEQ ID NO. 16); AEAKAEAKAEAKAEAK (SEQ ID NO. 17); AEAEAKAKAEAEAKAK (SEQ ID NO. 18); AEAEAEAEAKAKAKAK (SEQ ID NO. 19); RADARADARADARADA (SEQ ID NO. 20); RARADADARARADADA (SEQ ID NO. 21); SGRGYBLGGQGAGAAAAAGGAGQGGYGGLGSQG (SEQ ID NO. 22); EWEXEXEXEX (Where X=V, A, S, or P) (SEQ ID NO. 23); WKXKXKXKX (Where X=V, A, S, or P) (SEQ ID NO. 24); KWKVKVKVKVKVKVK (Where X=V, A, S, or P) (SEQ ID NO. 25); LLLLKKKKKKKKLLL (SEQ ID NO. 26); VKVKVKVKVDPPTKVKVKVKV (SEQ ID NO. 27); VKVKVKVKVDPPTKVKTKVKV (SEQ ID NO. 28); KVKVKVKVKDPPSVKVKVKVK (SEQ ID NO. 29); VKVKVKVKVDPPSKVKVKVKV (SEQ ID NO. 30); VKVKVKTKVDPPTKVKTKVKV (SEQ ID NO. 31); Fmoc-FF; Fmoc-GG; Fmoc-FG; KKSLSLSLSLSLSLKK (SEQ ID NO. 32); or YTIAALLSPY (SEQ ID NO. 33).

For example, the peptide A may be at least, at most or about 15, 20, 25, 30, 35, 40, 50, 60, 70, 80, 90, 100 amino acids in length, including all values and ranges there between. In further aspects, the peptide A may be at least, at most or about 7, 8, 9, 10, 11, 12, 13, 14, 15 to 15, 20, 25, 30, 35, 40, 50, 60, 70, 80, 90, 100 amino acids in length, including all values and ranges there between.

In certain aspects, one or more of the compounds attached to the non-13 sheet peptide tags (or peptide A) may be peptides, polypeptides, nucleic acids, small molecules, antigens, ligands, enzymes, reporters, drugs, matrices, cells, viruses, bacteria, lipids, carbohydrates, or a combination thereof.

For example, one or more of the compounds may be a peptide, same or different. In further aspects, at least one, two, three, four, more or all of the non-β-sheet peptide tags attached to a compound is a fusion protein. The non-β-sheet peptide tag (or peptide A) may be attached to the N and/C terminus of a peptide compound. In particular aspects, the non-β-sheet peptide tag (or peptide A) is attached to a peptide having 2 to 10,000 amino acids in length, more particularly 5, 10, 15, 20 to 15, 20, 30, 40, 50, 100, 200, 300, 400, 500, 1000 amino acids in length, including all values and ranges there between.

Non-limiting examples of a peptide compound attached to a non-β-sheet peptide tag (or peptide A) include an enzyme, fluorescent protein, cell binding domain, cell adhesion domain, extracellular matrix domain, reporter protein, cytokine, antigen, signaling domain, immunomodulating protein, cross-linking protein, hormone, hapten, or a combination thereof. In a particular example, extracellular matrix proteins or extracellular matrix protein domains may be used as the peptide compound or in the composition.

As used herein, the term "extracellular matrix", abbreviated "ECM", refers to the complex structural material that is produced by cells in mammalian tissues, particularly cells of connective tissue, for instance such cells as fibroblasts, osteoblasts, chondrocytes, epithelial cells, smooth muscle cells, adipocytes, and mesenchymal cells, and which material in vivo surrounds and supports those cells. Typically, the ECM is composed of fibres embedded in what is commonly referred to as 'ground substance'. ECM proteins include proteins in the fibers as structural proteins, such as collagen and/or elastin. Particularly suitable collagens are fibril-forming collagens. Type I collagen, type II collagen, type III collagen, type IV collagen or type X collagen are particularly preferred. A particular example is type I collagen.

ECM proteins also include proteins in the 'ground substance' of ECM, such as fibrillin, fibronectin, and/or laminin. Additional ECM proteins may include: glycoproteins such as laminin, entactin, tenascin, fibrillin, or fibronectin, for improving structural integrity of the network and for the attachment of cells to the ECM; osteocalcin (Gla protein), as a protein that binds calcium during mineralization; osteonectin, which serves a bridging function between collagen and mineral component; and sialoproteins, such as bone sialoprotein (BSP), osteopontin (OPN), dentin matrix protein-1 (DMP1), dentin sialophosphoprotein (DSPP) and matrix extracellular phosphoglycoprotein (MEPE).

When used in certain aspects, the term "extracellular matrix" or "extracellular matrix protein or protein domain" refers both to the material in vivo, as well as to the material in isolated form, separated from the cells that produced it. The ECM in certain aspects can be a natural or artificial material (e.g., a proteinaceous or peptide hydrogel).

In particular aspects, the compound attached to one or more of the non-β-sheet peptide tags (or peptide A) is an antigen. Antigens can be microbial antigens, such as viral, fungal, or bacterial; or therapeutic antigens such as antigens associated with cancerous cells or growths, including tumor antigens, or autoimmune disorders. In certain aspects, the antigens are peptides, lipids, carbohydrates, or other immunogenic molecules. The antigens can be T-cell and/or B-cell epitopes.

As used herein, the term "antigen" is a molecule capable of inducing an immune response or of being bound by an antibody or T-cell receptor. An antigen is additionally capable of inducing a humoral immune response and/or cellular immune response leading to the production of B- and/or T-lymphocytes. The structural aspect of an antigen that gives rise to a biological response is referred to herein as an "antigenic determinant." B-lymphocytes respond to foreign antigenic determinants via antibody production, whereas T-lymphocytes are the mediator of cellular immunity. Thus, antigenic determinants or epitopes are those parts of an antigen that are recognized by antibodies, or in the context of an MHC, by T-cell receptors. An antigenic determinant need not be a contiguous sequence or segment of protein and may include various sequences that are not immediately adjacent to one another. In particular aspects, the antigen may be an antigenic determinant or epitope.

In further aspects, the non-β-sheet peptide tags (or peptide A) and β-sheet peptides (or peptide B) may have a molar ratio of about 1:1, 1:2, 1:10, 1:50, 1:100, 1:200, 1:500, 1:1000, 1:2000, 1:5000, 1:10,000 50,000 to about 1:100,000 in the composition or the nanofiber structure, including all values and ranges there between.

In certain aspects, β-sheet peptides (or peptide B) comprise a plurality of self-assembling peptides. In other aspects the self-assembling peptides form a beta-sheet rich fibril. In further aspects, the self-assembling peptide comprises an amino acid sequence of QQKFQFQFEQQ (SEQ ID NO. 6); QQKFQFQFHQQ (SEQ ID NO. 7); FKFEFKFE (SEQ ID NO. 8); KFQFQFE (SEQ ID NO. 9); QQRFQFQFEQQ (SEQ ID NO. 10); QQRFQWQFEQQ (SEQ ID NO. 11); FEFEFKFK-FEFEFKFK (SEQ ID NO. 12); QQRFEWEFEQQ (SEQ ID NO. 13); QQXFXWXFQQQ (Where X denotes ornithine) (SEQ ID NO. 14); FKFEFKFEFKFE (SEQ ID NO. 15); FKFQFKFQFKFQ (SEQ ID NO. 16); AEAKAEAKAEA-KAEAK (SEQ ID NO. 17); AEAEAKAKAEAEAKAK (SEQ ID NO. 18); AEAEAEAEAKAKAKAK (SEQ ID NO. 19); RADARADARADARADA (SEQ ID NO. 20); RARADADARARADADA (SEQ ID NO. 21); SGRGY-BLGGQGAGAAAAAGGAGQGGYGGLGSQG (SEQ ID NO. 22); EWEXEXEXEX (Where X=V, A, S, or P) (SEQ ID NO. 23); WKXKXKXKXK (Where X=V, A, S, or P) (SEQ ID NO. 24); KWKVKVKVKVKVKVK (Where X=V, A, S, or P) (SEQ ID NO. 25); LLLLKKKKKKKKLLL (SEQ ID NO. 26); VKVKVKVKVDPPTKVKVKVKV (SEQ ID NO. 27); VKVKVKVKVDPPTKVKTKVKV (SEQ ID NO. 28); KVKVKVKVKDPPSVKVKVKVK (SEQ ID NO. 29); VKVKVKVKVDPPSKVKVKVKV (SEQ ID NO. 30); VKVKVKTKVDPPTKVKTKVKV (SEQ ID NO. 31); Fmoc-FF; Fmoc-GG; Fmoc-FG; KKSLSLSLSLSLSLKK (SEQ ID NO. 32); or YTIAALLSPY (SEQ ID NO. 33). In certain aspects, the self-assembling peptide is 2, 3, 4, 5, 6, 7, 8, 9, 10, 11, 12, 13, 14, 15 to 15, 20, 25, 30, 35, 40, 50, 100, 200, or 500 amino acids in length, including all values and ranges there between. In certain aspects, more than one self-assembling peptide is present in the composition.

In further aspects, the composition or nanostructure may be comprised in a pharmaceutically suitable carrier. For example, the composition may be further defined as an antigen composition. In other aspects, the composition may be in form of a microgel or further defined as microgel.

In further aspects, the composition may not be limited to microgels; particularly the composition may include any 3D structures at a microscopic scale or a macroscopic scale. For example, the composition may be a micro or macro structure with a size, length, diameter of at most, at least, or about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000 nm, μm, mm, cm or any range derivable therein. In certain aspects, the composition may be provided as a 3D cell culture or cell delivery matrix.

There may also be provided methods of providing the compositions described above. For example, the method may comprise mixing non-β-sheet peptide tags (or peptide A) and β-sheet peptides (or peptide B). In particular aspects, a non- β-sheet peptide tag is attached to a compound. In further aspects, same non-β-sheet peptide tag may be attached to same or different compounds as active agents. Therefore, there may be provided a nanofiber complex composition that forms a heterogeneous β-sheet structure comprising the non-β-sheet peptide tags and β-sheet peptides comprising different compounds. In further aspects, the method may further comprise shaking the mixture, thereby forming any form of cell culture or cell delivery matrix such as a microgel or a macrostructure.

The methods may involve a precise control of the concentration, temperature, or pH to achieve a nanostructure with a controlled dosage. For example, the pH may be at least, about, or at most 1, 2, 3, 4, 5, 6, 7, 8, 9, 10, 11, 12, 13, 14 or any range derivable therein. In particular aspects, the pH may be at about 7. The medium used in the methods may be any aqueous medium, such as phosphate buffered saline. In certain aspects, the peptide B or β-sheet peptides may be used at or above its fibrillizing concentration. For example, at least or about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000 mM or µM (or any range derivable therein) of the peptide A (or non-β-sheet peptides) or peptide B (or β-sheet peptides) may be used in the methods and compositions described herein.

Certain embodiments are directed to methods of inducing an immune response comprising administering an effective amount of a composition comprising one or more antigens. In further aspects, the method may be provided for treating a patient having or at risk of developing a microbial infection by administering to the patient an effective amount of a composition described herein. In certain aspects, there may be provided methods of treating a patient having or at risk of developing a cancer, comprising administering to the patient an immunotherapy comprising an effective amount of a composition described herein. In further aspects, there may be provided a method of culturing a cell, comprising incubating the cell in a cell culture medium comprising the composition described herein, particularly a macroscopic structure or a microgel composition.

Certain methods and compositions may also be provided for cell delivery, for example, by culturing or suspending cells in the composition provided herein for a period, and then delivering the cells to a tissue or a patient or subject. The composition described herein may be formulated into a cell delivery matrix, for example including ECM proteins or protein domains, particularly from the patient's own body. Methods of delivering cells to a subject include delivering the cell delivery composition to particular tissue sites. For instance, the tissue site may include epithelial, connective, skeletal, muscular, glandular, or nervous tissue. A particular tissue site is cardiac tissue. In an additional aspect of the method, the subject may be a mammal, and in a further aspect the mammal may be a human. One advantage of the cell delivery methods and compositions may be to improve the survival and function of the cells when delivered in vivo. In a particular aspect, at least, at most or about 50, 60, 70, 80, 90, 95, 99% or more (or any range derivable therein) of the cells remain viable after delivery to a tissue site. In a further aspect, the cells are delivered to the tissue site at a constant rate.

Methods may involve administering to the patient or subject at least or at most 1, 2, 3, 4, 5, 6, 7, 8, 9, 10 or more doses of a pharmaceutical composition or a composition described herein. A dose may be a composition comprising about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 milligrams (mg) or micrograms (mcg) or µg/ml or micrograms/ml or mM or µM (or any range derivable therein) of each compound or the total amount of a combination of compounds or the compositions.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 (A-E): An engineered fusion protein with a β-sheet fibrillizing tail (a "βTail) integrated into nanofibers of β-sheet fibrillizing peptides in a βTail-dependent manner, without loss of activity. a) Schematic representation of a βTail fusion protein integrating into Q11 nanofibers. b-c) βTail underwent slow secondary structural transition from an α-helix to a β-sheet. d-e) A fusion of βTail and Green Fluorescent Protein-UV (βT-GFPuv) integrated into Q11, HK-Q11 and KFE8 nanofibers in a βTail-dependent manner. N=3, mean±s.d. for e. * represents p<0.05, ANOVA with Tukey's post-hoc. GFP adapted from PDB 1EMA in a.

FIG. 1 (A-F): Engineered fusion proteins with a β-sheet fibrillizing tail that integrated into nanofibers of β-sheet fibrillizing peptides. FIG. 1A) Schematic representation of engineered fusion proteins having a β-sheet fibrillizing domain integrating into Q11 nanofibers. FIG. 1B-C) The βTail peptide underwent slow secondary structural transition from an α-helix to a β-sheet, whereas Q11 rapidly assembled into β-sheets, and a mutated βTail adopted a random coil structure. A fusion of βTail and Green Fluorescent Protein-UV (βT-GFP) efficiently integrated into Q11 nanofibers, whereas a fusion of Q11 and GFP (Q11-GFP) integrated moderately, and a fusion of GFP and a non-folding βTail mutant (βTmutant-GFP) integrated poorly, as demonstrated by (FIG. 1D) digital photographs, and (FIG. 1E) measured by fluorimetry of the supernatant above sedimented Q11 nanofiber solutions. FIG. 1F) βT-GFP also integrated into HK-Q11 and KFE8 nanofibers in a βTail-dependent manner, indicating that co-assembly was not limited to Q11-based nanofibers. N=3, mean±s.d. for e and f. * represents p<0.05, ANOVA with Tukey's post-hoc. GFP adapted from PDB 1EMA in FIG. 1A.

FIG. 2A) βT-GFPuv integrated into Q11 nanofibers over the range of 0.25-1.5 μM in a βTail-dependent manner, as measured by loss of fluorescence from the supernatant. FIG. 2B) βT-GFPuv integrated into Q11 gels in a βTail-dependent manner without loss of activity. FIG. 2C) Active βTail-GFP dose in Q11 gels correlated with βT-GFPuv concentration in solution during assembly. FIG. 2D) Different fluorescent βTail proteins co-integrated into Q11 gels at a precise molar ratio, as demonstrated by the close correlation between actual gel color and the predicted color, which was determined by using the protein mole ratio in solution during assembly as the RGB pixel ratio. N=3, mean±s.d. for FIG. 2A, N=10, mean±s.d. for FIG. 2C.

FIG. 3A) A fusion of βTail and the fungal enzyme cutinase (βT-cut) integrated into Q11 nanofibers over the range of 0.25-1.5 μM in a βTail-dependent manner, as measured by loss of protein from the supernatant. FIG. 3B) Q11 nanofibers assembled in the presence of βT-cut demonstrated cutinase activity, as measured by hydrolysis of p-nitrophenyl butyrate (colorless) to p-nitrophenol (yellow). FIG. 3C) Nanofiber cutinase activity was precisely varied by changing the concentration of βT-cut present during Q11 assembly. FIG. 3D) βT-GFPuv and βT-cut co-integrated into Q11 nanofibers at a predictable ratio without loss of activity, as demonstrated by the direct correlation between nanofiber fluorescence or cutinase activity and βT-GFPuv or βT-cut concentration, respectively. N=3, mean±s.d.

FIG. 4A) TEM identified gold-labeled 2° antibodies bound to Q11 nanofibers assembled in the presence of βT-GFPuv and incubated with an anti-GFP 1° antibody, whereas few gold-labeled antibodies bound to Q11 assembled in the presence of a βTail peptide and incubated with anti-GFP. FIG. 4B) TEM identified gold-labeled streptavidin bound to Q11 nanofibers assembled in the presence of biotinylated βTail, whereas few gold beads were co-localized with Q11 nanofibers lacking biotinylated-βTail. FIG. 4C) Tryptophan-terminated βTail (W-βT) integrated into Q11 nanofibers over the range of 25-100 μM in a βTail-dependent manner, as measured by loss of fluorescence from the supernatant. FIG. 4D-E) βTail secondary structure changed from α-helical to β-sheet following overnight co-assembly with Q11 at a 1:10 molar ratio, whereas βTmutant secondary structure was unchanged in the presence of a 10-fold molar excess of Q11. N=3, mean±s.d. for c.

FIG. 5A) Higher anti-GFP total IgG titers were raised by C57BL/6 mice immunized with βT-GFPuv integrated into Q11 nanofibers when compared to titers raised following immunization with soluble βT-GFPuv. FIG. 5B) Q11 nanofibers bearing βT-GFPuv elicited robust serum Ig isotype switching to predominantly IgG1, whereas soluble βT-GFPuv elicited a more balanced IgG1/IgM profile after primary and booster immunizations. FIG. 5C) Higher anti-cut total IgG titers were raised by C57BL/6 mice immunized with βTail-cut integrated into Q11 nanofibers when compared to titers raised following immunization with soluble βTail-cut. N=5, mean±s.d. * represents p<0.05, Student's t-test (FIG. 5A, C), or ANOVA with Tukey's post-hoc (FIG. 5B), serum titer=1 (dashed line) indicates no detectable antibodies.

FIG. 8A) Nanofibers were identified in solutions containing 1 mM HK-Q11 in PBS with TEM. FIG. 8B)

The fluorescence of thioflavin T, a fluorescent dye whose emission increases upon binding to β-sheet fibrils, increased in solutions containing HK-Q11.

Figure 9:
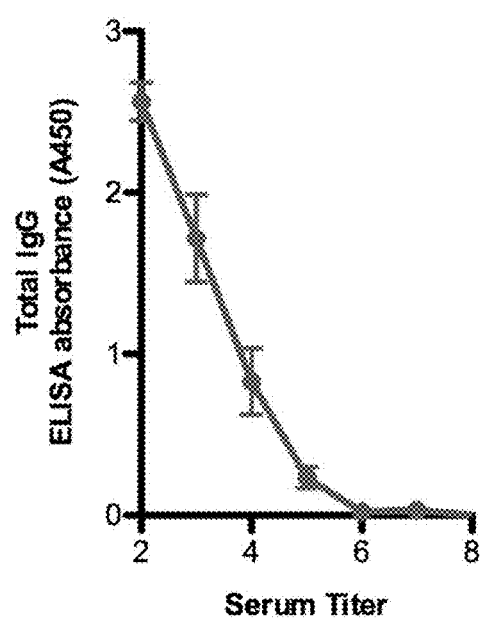
Figure 10:
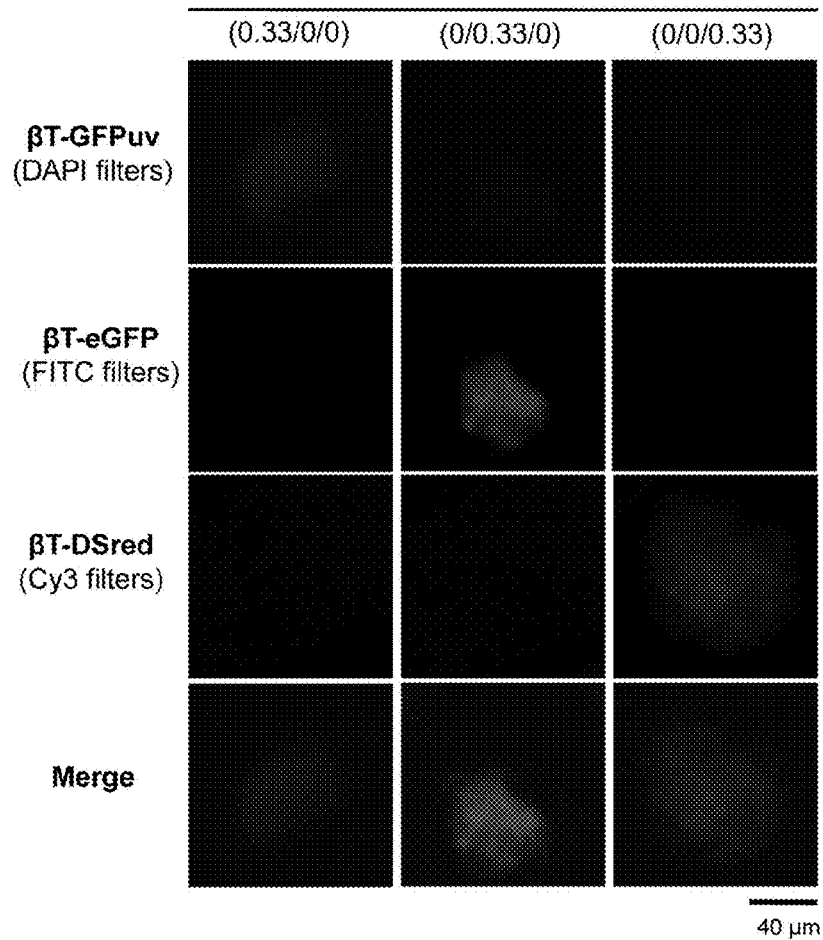

FIG. 9: Endotoxin is not a key mediator of adaptive immune responses elicited by nanofibers bearing BT-GFPuv. Total anti-GFP IgG, measured by ELISA, raised by TLR4 knock-out C57BL/6 mice 7 weeks after primary and booster immunization with Q11 and BT-GFPuv (1 mM Q11; primary=90 nmol and booster=80 nmol βTail-GFPuv). N=5, mean±s.e.m.

FIG. 10: Fluorescence emission from βTail-GFPuv, βTail-eGFP, and βTail-dsRED was distinguishable with different fluorescence filter cubes. Exposure times of 0.75 s for βTail-GFPuv, 1.5 s for βTail-eGFP, and 2.5 s for βTail-dsRED enabled visualization of each protein, without significant background fluorescence from the other proteins.

DESCRIPTION OF ILLUSTRATIVE EMBODIMENTS

Certain embodiments are, in part, based on the finding that engineered fusion proteins having a peptide tag such as a β-sheet fibrillizing tail (a "βTail") integrated into nanofibers of β-sheet fibrillizing polypeptides at a tunable dose, without loss of bioactivity. Further, the inventors discovered that multiple different βTail fusion proteins co-integrated into polypeptide nanofibers, providing biomaterials with modular and precise composition of bioactive proteins. One aspect also involves compositions and methods related to the use of protein-bearing nanofibers as self-adjuvanting vaccines, immunogenic compositions or cell culture medium or structure, with the potential of this approach for creating biomaterials with unique functional properties for various biomedical and biotechnological applications, such as therapeutics, tissue engineering, drug delivery, 3-D culture, biosensors, or electronics.

I. NON-β-SHEET PEPTIDE TAGS

Embodiments involve the use of non-β-sheet peptide tags. The peptides may form random coil, α-helical structure or β-sheet structure under different conditions. In particular embodiments, the peptide tags may form β-sheet structure in the presence of a β-sheet peptide such as a β-sheet fibrillizing peptide, including self-assembly peptides described below. When isolated or expressed, the peptide tag may form non-β-sheet structures, such as random coil or α-helical structures (e.g., Pagel 2006, incorporated herein by reference).

Such peptide tags may have one or more α-helical motifs or coiled coil motifs, such as heptad repeats. A coiled coil is a structural motif in proteins. The motif may form a plurality of alpha-helices that are coiled together like the strands of a rope (dimers and trimers are the most common types). In particular aspects, the peptides may have intact or modified heptad repeats as described below for forming α-helical structures or favor forming α-helical structures and also β-sheet forming amino acids or amino acids or amino acids that increase the β-sheet formation propensity.

The α-helical motifs may contain a repeated pattern, hxxhcxc, of hydrophobic (h) and charged (c) amino-acid residues, referred to as a heptad repeat. The positions in the heptad repeat may be labeled abcdefg, where a and d are the hydrophobic positions, for example being occupied by isoleucine, leucine or valine, b, c, f are likely hydrophilic or polar residues, and e and g are likely charged resides. Using this nomenclature, each heptad may start with any of a, b, c, d, e, f or g (or a', b', c', d', e', f' or g'), not necessarily a or a'. For example, the heptad repeat may be denoted $(a\text{-}b\text{-}c\text{-}d\text{-}e\text{-}f\text{-}g)_n$ or $(g\text{-}a\text{-}b\text{-}c\text{-}d\text{-}e\text{-}f)_n$. For example, n may be from about 2, 3, 4, 5, 6, 7, 8, 9 to about 10 or more.

In certain embodiments, positions a and/or d may be leucine (L). In further embodiments, positions e and g may be a pair of charged resides, such as lysine (K) and glutamic acid (E), or glutamic acid (E) and lysine (K), histidine (H) and glutamic acid (E), glutamic acid (E) and histidine (H), arginine (R) and glutamic acid (E), glutamic acid (E) and arginine (R), lysine (K) and aspartic acid (D), aspartic acid (D) and lysine (K), histidine (H) and aspartic acid (D), aspartic acid (D) and histidine (H), arginine (R) and aspartic acid (D) or any other similarly pairs with opposing charges or without opposing charges. In an embodiment, a heptad repeat may have a sequence of (L E K L K S E) ((SEQ ID NO. 34), (L V V L H S E) (SEQ ID NO. 35), or (L H K L K S E) (SEQ ID NO. 36).

Because positions b, c, and f are solvent exposed, these positions only have a minor impact on α-helical or coiled-coil stability. These positions may be any amino acids, such as glutamic acid (E), lysine (K), histidine (H), serine (S), or valine (V). In particular aspects, these positions may comprise one or more β-sheet forming amino acids or amino acids that increase β-sheet formation propensity compared to its absence. Such amino acids may include, but are not limited to glycine, alanine, valine, leucine, and isoleucine, and other non-naturally occurring amino acids which may be used in a similar chemical and structural manner in the peptides.

In further embodiments, the peptide tags may comprise or may not need one or more metal binding sites that may stabilize or disrupt the helical structure or sheet structure. In particular embodiments, the heptad repeats may have one or more metal binding sites introduced in an i, i+4 geometry that stabilizes the helical structure. For example, two metal binding sites, such as histidine (H), may be incorporated into two neighboring heptad repeats. Such metal binding sites may be close enough to each other in the α-helical conformation to help induce or stabilize the α-helical structure and/or slow down the transition to a β-sheet structure.

The peptide tags may comprise from 2 to about 200 (e.g. about 3 to about 100, such as about 3, 4, 5, 6, 7, 8, 9, 10, 20, 30, 40 or 50 or any intermediate ranges) heptad repeats, or particularly 3, 4, 5, 6, 7, 8, 9 or 10 heptads. Two or more of the heptads may contain the same repeating sequence of seven amino acids. Alternatively, each heptad in the peptide tags may be the same or each may be different.

Folding a sequence with this repeating pattern into an alpha-helical secondary structure may cause the hydrophobic residues to be presented as a "stripe" that coils gently around the helix in left-handed fashion, forming an amphipathic structure. The more favorable way for two such helices to arrange themselves in the water-filled environment of the cytoplasm is to wrap the hydrophobic strands against each other sandwiched between the hydrophilic amino acids. It is thus the burial of hydrophobic surfaces that provides the thermodynamic driving force for the oligomerization. The packing in a coiled-coil interface may be exceptionally tight, with almost complete van der Waals contact between the side chains of the a and d residues.

The α-helices may be parallel or anti-parallel, and may adopt a left-handed super-coil. Although disfavored, a few right-handed α-helices or coiled coils have also been observed in nature and in designed proteins.

II. NANOFIBERS

Mixing or co-assembly of β-sheet fibrillizing polypeptides that contain a population of peptide tags (particularly referring to a peptide that can form both α-helical structures and β-sheet structures under different conditions) with a different population of β-sheet peptides (a different peptide) may be used to prepare nanofibers, microgels, or scaffolds in certain aspects of the present invention.

Without limitation one or more β-sheet fibrillizing polypeptides comprising different molecules such as antigens may be used to prepare the scaffolds, microgels, and nanofibers. The amount of β-sheet fibrillizing polypeptides comprising non-β-sheet peptides and antigens compared to the β-sheet peptides maybe varied without limitation in the preparation of the scaffolds, microgels, and nanofibers.

The mixture of first and second peptides may be incubated under any conditions suitable for forming nanofibers, microgels, or scaffolds. For example, the condition may be an aqueous medium, a rocking platform, or a combination thereof. The nanofiber may include any forms of nanostructures comprising β-sheet secondary structures, such as a nanofibril, a nanowire, a nanosurface and a nanosphere.

The self-assembled micelles and nanofibers may be characterized by NOE and FT-IR spectroscopy, circular dichroism; nanofiber fiber networks may be visualized using transmission electron microscopy (TEM).

III. SELF-ASSEMBLING PEPTIDES

Certain aspects include self-assembling peptides, which may be used in β-sheet peptides (or peptide B) or polypeptides. Non-limiting examples of self-assembling peptides have been described in US Patent Publication 2012-0282292, which is incorporated herein by reference by its entirety.

As used herein, the term "self-assembling peptide" refers to peptides that are able to spontaneously associate and form stable structures. In one embodiment, a self-assembling peptide comprises an amino acid sequence of QQKFQFQFEQQ (SEQ ID NO. 6); QQKFQFQFHQQ (SEQ ID NO. 7); FKFEFKFE (SEQ ID NO. 8); KFQFQFE (SEQ ID NO. 9); QQRFQFQFEQQ (SEQ ID NO. 10); QQRFQWQFEQQ (SEQ ID NO. 11); FEFEFKFKFEFEFKFK (SEQ ID NO. 12); QQRFEWEFEQQ (SEQ ID NO. 13); QQXFXWXFQQQ (Where X denotes ornithine) (SEQ ID NO. 14); FKFEFKFEFKFE (SEQ ID NO. 15); FKFQFKFQFKFQ (SEQ ID NO. 16); AEAKAEAKAEAKAEAK (SEQ ID NO. 17); AEAEAKAKAEAEAKAK (SEQ ID NO. 18); AEAEAEAEAKAKAKAK (SEQ ID NO. 19); RADARADARADARADA (SEQ ID NO. 20); RARADADARARADADA (SEQ ID NO. 21); SGRGYBLGGQGAGAAAAAGGAGQGGYGGLGSQG (SEQ ID NO. 22); EWEXEXEXEX (Where X=V, A, S, or P) (SEQ ID NO. 23); WKXKXKXKXK (Where X=V, A, S, or P) (SEQ ID NO. 24); KWKVKVKVKVKVKVK (SEQ ID NO. 25); LLLLKKKKKKKKLLLL (SEQ ID NO. 26); VKVKVKVKVDPPTKVKVKVKV (SEQ ID NO. 27); VKVKVKVKVDPPTKVKTKVKV (SEQ ID NO. 28); KVKVKVKVKDPPSVKVKVKVK (SEQ ID NO. 29); VKVKVKVKVDPPSKVKVKVKV (SEQ ID NO. 30); VKVKVKTKVDPPTKVKTKVKV (SEQ ID NO. 31); Fmoc-FF; Fmoc-GG; Fmoc-FG; KKSLSLSLSLSLSLKK (SEQ ID NO. 32); or YTIAALLSPY (SEQ ID NO. 33) or conservatively modified variants thereof. Self-assembling peptides may further comprise other compounds, for example, immunogenic peptides.

Certain peptides that comprise of alternating hydrophilic and hydrophobic amino acids self-assemble to form an exceedingly stable beta-sheet macroscopic scaffold (U.S. Pat. Nos. 5,955,343 and 5,670,483, each of which is incorporated herein by reference).

Many self-complementary peptides have identical compositions and length; such as EAK16, KAE16, RAD16, RAE16, and KAD16 have been exemplified below (Table 1).

TABLE 1

Representative Self-Assembling peptides

| Name | Sequence (n- -> c) | SEQ ID NO: | Modulus | Structure |
|---|---|---|---|---|
| RADA16-I | n-RADARADARADARADA-c | 20 | I | β |
| RGDA16-I | n-RADARGDARADARGDA-c | 37 | I | r.c |
| RADA8-I | n-RADARADA-c | 38 | I | r.c. |
| RAD16-II | n-RARADADARARADADA-c | 21 | II | β |
| RAD8-II | n-RARADADA-c | 39 | II | r.c. |
| EAKA16-I | n-AEAKAEAKAEAKAEAK-c | 17 | I | β |
| EAKA8-I | n-AEAKAEAK-c | 40 | I | r.c. |
| RAEA16-I | n-RAEARAEARAEARAEA-c | 41 | I | β |
| RAEA8-I | n-RAEARAEA-c | 42 | I | r.c. |
| KADA16-I | n-KADAKADAKADAKADA-c | 43 | I | β |
| KADA8-I | n-KADAKADA-c | 44 | I | r.c. |
| EAH16-II | n-AEAEAHAHAEAEAHAHA-c | 45 | II | β |
| EAH8-II | n-AEAEAHAHA-c | 46 | II | r.c. |
| EFK16-II | n-FEFEFKFKFEFEFKFK-c | 12 | II | β |
| EFK8-II | n-FEFKFEFK-c | 47 | I | β |
| ELK16-II | n-LELELKLKLELELKLK-c | 48 | II | β |
| ELK8-II | n-LELELKLK-c | 49 | II | r.c. |
| EAK16-II | n-AEAEAKAKAEAEAKAK-c | 18 | II | β |
| EAK12 | n-AEAEAEAEAKAK-c | 50 | IV/II | α/β |
| EAK8-II | n-AEAEAKAK-c | 51 | II | r.c. |
| KAE16-IV | n-KAKAKAKAEAEAEAEA-c | 52 | IV | β |
| EAK16-IV | n-AEAEAEAEAKAKAKAK-c | 19 | IV | β |
| RAD16-IV | n-RARARARADADADADA-c | 53 | IV | β |
| DAR16-IV | n-ADADADADARARARAR-c | 54 | IV | α/β |
| DAR16-IV* | n-DADADADARARARARA-c | 55 | IV | α/β |
| DAR32-IV | n-ADADADADARARARAR-c | 56 | IV | α/β |
| EHK16 | n-HEHEHKHKHEHEHKHK-c | 57 | N/A | r.c. |
| EKH8-I | n-HEHEHKHK-c | 58 | N/A | r.c. |
| VE20* | n-VEVEVEVEVEVEVEVEVEVE-c | 59 | N/A | β |
| RF20* | n-RFRFRFRFRFRFRFRFRFRF-c | 60 | N/A | β |

β denotes beta-sheet;
α denotes alpha-helix;
r.c. denotes random coil;
N/A denotes not applicable.
*Both VE20 and RF20 form a beta-sheet when they are incubated in a solution containing NaCl; however, they do not self-assemble to form macroscopic scaffolds.

The peptides described herein can be chemically synthesized using standard chemical synthesis techniques. In some embodiments the peptides are chemically synthesized by any of a number of fluid or solid phase peptide synthesis techniques known to those of skill in the art. Solid phase synthesis in which the C-terminal amino acid of the sequence is attached to an insoluble support followed by sequential addition of the remaining amino acids in the sequence is a preferred method for the chemical synthesis of the polypeptides of this invention. Techniques for solid phase synthesis are well known to those of skill in the art and are described, for example, by Barany and Merrifield (1963) Solid-Phase Peptide Synthesis; pp. 3-284 in The Peptides: Analysis, Synthesis, Biology. Vol. 2: Special Methods in Peptide Synthesis, Part A.; Merrifield et al. (1963) J. Am. Chem. Soc., 85: 2149-2156, and Stewart et al. (1984) Solid Phase Peptide Synthesis, 2nd ed. Pierce Chem. Co., Rockford, Ill.

IV. COMPOUNDS

Certain embodiments comprise incorporating one or more different compounds into a β-sheet assembly via a non-β-sheet peptide that transitions into a β-sheet structure in the presence of β-sheet peptides. The compound can be any biocompatible molecules, like a small molecule, a drug, a peptide, a lipid, a sugar molecule, or a cell, or any bio-compatible material such as a matrix, a gel, membrane, micelle, or fiber. In particular embodiments, the compound may be an antigen. As used herein, the term "biocompatible" refers to a substance which produces no significant untoward effects when applied to, or administered to, a given cell or organism according to the methods and amounts described herein.

A. Compounds

In certain embodiments, the compound may be a peptide. A peptide may be any peptide or polypeptide, including, but not be limited to, an enzyme, fluorescent protein, cell-binding domain, cell adhesion domain, extracellular matrix domain, reporter protein, cytokine, antigen, signaling domain, immunomodulating protein, cross-linking protein, hormone, hapten, or a bioactive ligand, such as a peptide, protein, or nucleic acid.

In further embodiments, the compound includes or is substantially in the form of at least one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, glycopeptide, glycolipid, lipoprotein, sphingolipid, glycosphingolipid, glycoprotein, peptidoglycan, lipid, carbohydrate, metalloprotein, proteoglycan, chromosome, nucleus, acid, support structure, buffer, protic solvent, aprotic solvent, nitric oxide, nitrous oxide, nitric oxide synthase, amino acid, micelle, polymer, copolymer, monomer, prepolymer, cell receptor, adhesion molecule, cytokine, chemokine, immunoglobulin, antibody, antigen, platelet, extracellular matrix, blood, plasma, cell ligand, zwitterionic material, cationic material, oligonucleotide, nanotube, piloxymer, transfersome, gas, element, contaminant, radioactive particle, hormone, microorganism, bacteria, virus, quantum dot, contrast agent, or any part thereof.

B. Antigens

The term "antigen" may refer to a molecule against which a subject can initiate a humoral and/or cellular immune response. Antigens can be any type of biologic molecule including, for example, simple intermediary metabolites, sugars, lipids, and hormones as well as macromolecules such as complex carbohydrates, phospholipids, nucleic acids and proteins.

Common categories of antigens include, but are not limited to, viral antigens, bacterial antigens, fungal antigens, protozoa and other parasitic antigens, tumor antigens, antigens involved in autoimmune disease, allergy and graft rejection, and other miscellaneous antigens. In certain compositions and methods, the antigen is a peptide.

Viral Antigens.

Examples of viral antigens include, but are not limited to, retroviral antigens such as retroviral antigens from the human immunodeficiency virus (HIV) antigens such as gene products of the gag, pol, and env genes, the Nef protein, reverse transcriptase, and other HIV components; hepatitis viral antigens such as the S, M, and L proteins of hepatitis B virus, the pre-S antigen of hepatitis B virus, and other hepatitis, e.g., hepatitis A, B. and C, viral components such as hepatitis C viral RNA; influenza viral antigens such as hemagglutinin and neuraminidase and other influenza viral components; measles viral antigens such as the measles virus fusion protein and other measles virus components; rubella viral antigens such as proteins E1 and E2 and other rubella virus components; rotaviral antigens such as VP7sc and other rotaviral components; cytomegaloviral antigens such as envelope glycoprotein B and other cytomegaloviral antigen components; respiratory syncytial viral antigens such as the RSV fusion protein, the M2 protein and other respiratory syncytial viral antigen components; herpes simplex viral antigens such as immediate early proteins, glycoprotein D, and other herpes simplex viral antigen components; varicella zoster viral antigens such as gpI, gpII, and other varicella zoster viral antigen components; Japanese encephalitis viral antigens such as proteins E, M-E, M-E-NS1, NS1, NS1-NS2A, 80% E, and other Japanese encephalitis viral antigen components; rabies viral antigens such as rabies glycoprotein, rabies nucleoprotein and other rabies viral antigen components. See Fundamental Virology, Second Edition, e's. Fields, B. N. and Knipe, D. M. (Raven Press, New York, 1991) for additional examples of viral antigens.

Bacterial Antigens.

Bacterial antigens which can be used include, but are not limited to, pertussis bacterial antigens such as pertussis toxin, filamentous hemagglutinin, pertactin, FIM2, FIM3, adenylate cyclase and other pertussis bacterial antigen components; diptheria bacterial antigens such as diptheria toxin or toxoid and other diphtheria bacterial antigen components; tetanus bacterial antigens such as tetanus toxin or toxoid and other tetanus bacterial antigen components; streptococcal bacterial antigens such as M proteins and other streptococcal bacterial antigen components; gram-negative bacilli bacterial antigens such as lipopolysaccharides and other gram-negative bacterial antigen components; *Mycobacterium tuberculosis* bacterial antigens such as mycolic acid, heat shock protein 65 (HSP65), the 30 kDa major secreted protein, antigen 85A and other mycobacterial antigen components; *Helicobacter pylori* bacterial antigen components; pneumococcal bacterial antigens such as pneumolysin, pneumococcal capsular polysaccharides and other pneumococcal bacterial antigen components; hemophilus influenza bacterial antigens such as capsular polysaccharides and other hemophilus influenza bacterial antigen components; anthrax bacterial antigens such as anthrax protective antigen and other anthrax bacterial antigen components; rickettsiae bacterial antigens such as romps and other rickettsiae bacterial antigen component. Also included with the bacterial antigens described herein are any other bacterial, mycobacterial, mycoplasmal, rickettsial, or chlamydial antigens.

Fungal Antigens.

Fungal antigens which can be used in the compositions and methods include, but are not limited to, Candida fungal antigen components; histoplasma fungal antigens such as heat shock protein 60 (HSP60) and other histoplasma fungal antigen components; cryptococcal fungal antigens such as capsular polysaccharides and other cryptococcal fungal antigen components; coccidiodes fungal antigens such as spherule antigens and other coccidiodes fungal antigen components; and tinea fungal antigens such as trichophytin and other coccidiodes fungal antigen components.

Parasite Antigens.

Examples of protozoa and other parasitic antigens include, but are not limited to, plasmodium falciparum antigens such as merozoite surface antigens, sporozoite surface antigens, circumsporozoite antigens, gametocyte/gamete surface antigens, blood-stage antigen pf 1 55/RESA and other plasmodial antigen components; toxoplasma antigens such as SAG-1, p30 and other toxoplasma antigen components; schistosomae antigens such as glutathione-S-transferase, paramyosin, and other schistosomal antigen components; leishmania major and other leishmaniae antigens such as gp63, lipophosphoglycan and its associated protein and other leishmanial antigen components; and trypanosoma cruzi antigens such as the 75-77 kDa antigen, the 56 kDa antigen and other trypanosomal antigen components.

Tumor Antigens.

Tumor antigens which can be used in the compositions and methods include, but are not limited to, telomerase components; multidrug resistance proteins such as P-glycoprotein; MAGE-1, alpha fetoprotein, carcinoembryonic antigen, mutant p53, immunoglobulins of B-cell derived malignancies, fusion polypeptides expressed from genes that have been juxtaposed by chromosomal translocations, human chorionic gonadotrpin, calcitonin, tyrosinase, papillomavirus antigens, gangliosides or other carbohydrate-containing components of melanoma or other tumor cells. It is contemplated in certain embodiments that antigens from any type of tumor cell can be used in the compositions and methods described herein.

Antigens Relating to Autoimmunity.

Antigens involved in autoimmune diseases, allergy, and graft rejection can be used in certain aspects. For example, an antigen involved in any one or more of the following autoimmune diseases or disorders can be used in the present invention: diabetes mellitus, arthritis (including rheumatoid arthritis, juvenile rheumatoid arthritis, osteoarthritis, psoriatic arthritis), multiple sclerosis, myasthenia gravis, systemic lupus erythematosis, autoimmune thyroiditis, dermatitis (including atopic dermatitis and eczematous dermatitis), psoriasis, Sjogren's Syndrome, including keratoconjunctivitis sicca secondary to Sjogren's Syndrome, alopecia greata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Crohn's disease, Graves opthalmopathy, sarcoidosis, primary biliary cirrhosis, uveitis posterior, and interstitial lung fibrosis. Examples of antigens involved in autoimmune disease include glutamic acid decarboxylase 65 (GAD 65), native DNA, myelin basic protein, myelin proteolipid protein, acetylcholine receptor components, thyroglobulin, and the thyroid stimulating hormone (TSH) receptor. Examples of antigens involved in allergy include pollen antigens such as Japanese cedar pollen antigens, ragweed pollen antigens, rye grass pollen antigens, animal derived antigens such as dust mite antigens and feline antigens, histocompatibility antigens, and penicillin and other therapeutic drugs. Examples of antigens involved in graft rejection include antigenic components of the graft to be transplanted into the graft recipient such as heart, lung, liver, pancreas, kidney, and neural graft components. An antigen can also be an altered peptide ligand useful in treating an autoimmune disease.

Examples of miscellaneous antigens which can be can be used in certain aspects include endogenous hormones such as luteinizing hormone, follicular stimulating hormone, testosterone, growth hormone, prolactin, and other hormones, drugs of addiction such as cocaine and heroin, and idiotypic fragments of antigen receptors such as Fab-containing portions of an anti-leptin receptor antibody.

C. ECM Proteins or Protein Domains

The compounds may include a cell attachment molecule comprising amino acids, which is an extracellular matrix (ECM) protein, or a peptide that includes an ECM protein domain. As known in the art, ECM proteins provide structural support to cells and/or attach cells that reside in the ECM. Molecules on the surface of cells, such as integrins, carbohydrates, and other cell adhesion molecules can interact with ECM proteins to promote cell attachment. Non-limiting exemplary ECM proteins include fibronectin, laminin, collagen, procollagen, elastin, vitronectin, tenascin, entactin, fibrinogen, thrombospondin, osteopontin (bone sialoprotein), osteocalcin, von Willibrand Factor, and active domains thereof.

ECM protein domains refer to an amino acid sequence found within the ECM protein that, in itself, provides function according to one or more properties of the ECM protein, such as providing structural support to cells and/or for attaching cells. The domain may also be referred to as a "active portion" or "motif." The peptide that includes an ECM protein domain can have a "core sequence" of amino acid residues, and optionally one or more additional amino acid residues that flank (i.e., on the C-terminus, N-terminus, or both) the core sequence. The one or more additional amino acids that flank the core sequence can correspond to the wild type ECM sequence in the relevant region of the protein, or can be an amino acid(s) that diverges from the wild type sequence (e.g., a "variant amino acid or sequence"). The variant amino acid or sequence can be one that enhances properties of the peptide, such as providing enhanced ligand interaction, and/or can facilitate formation of the second coated layer.

ECM protein domains are known in the art or can be determined using routine experimentation by carrying out assays that are commercially or described in a reference. For example, cell attachment assays which utilize peptides or proteins adhered to plastic or covalently immobilized on a support have been described and can be used to determine the activity of a desired peptide for promoting attachment of cells (see, for example, Malinda, K. M., et al. (1999) FASEB J. 13:53-62; or Kato, R., et al. (2006) J. Biosci. Bioeng. 101: 485-95).

V. PHARMACEUTICAL COMPOSITIONS

Embodiments of the present invention include pharmaceutical compositions comprising the compositions of nanostructures prepared as above and methods for using these compositions. These compositions may be pharmaceutical compositions used in preventive care or therapeutics.

For example, the compositions may be immunogenic compositions used for preventing or ameliorating microbial infections. A particular application is prophylaxis for infectious diseases. Exposure to antigens in the nanostructure can create resistance against such diseases or act as a vaccination for various conditions.

In other embodiments, the compositions may be immunogenic compositions used in immunotherapy, such as a cancer immunotherapy. The antigens used may be antigens that are displayed on tumor cells but not healthy cells. Several antigens have been identified as specific to certain types of tumors, such as Caspase-8, MAGE-I, Tyrosinase, HER-2/neu, and MUC-I. With this in mind, nano structures can be used to deliver such antigens to DCs in lymph nodes as a means for activating T cells to attack tumors. The compositions may be administered to a subject or cells in vivo or cells in vitro. The cells may be immune cells, such as T cells, B cells, NK cells, or any other immune cells.

As such, certain aspects contemplate vaccines and therapeutics for use in active immunization of subjects. Pharmaceutical compositions such as immunogenic compositions can include a β-sheet peptide fibril integrated with non-β-sheet peptide tags coupled to a plurality of antigens, "fibril complex."

The preparation of pharmaceutical compositions such as vaccine compositions that contain polypeptide or peptide sequence(s) as active ingredients is generally well understood in the art, as exemplified by U.S. Pat. Nos. 4,608,251; 4,601,903; 4,599,231; 4,599,230; 4,596,792; and 4,578,770, all of which are incorporated herein by reference. For example, such pharmaceutical may be prepared as injectables either as liquid solutions or suspensions: solid forms suitable for solution in or suspension in liquid prior to injection may also be prepared. The preparation may also be emulsified.

The active immunogenic ingredient is often mixed with excipients that are pharmaceutically acceptable and compatible with the active ingredient. Suitable excipients are, for example, water, saline, dextrose, glycerol, ethanol, or the like and combinations thereof. In addition, if desired, the pharmaceutical composition such as vaccine may contain amounts of auxiliary substances such as wetting or emulsifying agents, pH buffering agents, or adjuvants that enhance the effectiveness of the compositions. In specific embodiments, vaccines are formulated with a combination of substances, as described in U.S. Pat. Nos. 6,793,923 and 6,733,754, which are incorporated herein by reference.

Pharmaceutical compositions may be conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides: such suppositories may be formed from mixtures containing the active ingredient in the range of about 0.5% to about 10%, preferably about 1% to about 2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10% to about 95% of active ingredient, preferably about 25% to about 70%.

Upon formulation, compositions may be administered in a manner compatible with the dosage formulation, and in such amount as will be therapeutically effective and/or immunogenic. The formulations are easily administered in a variety of dosage forms. The quantity to be administered depends on the subject to be treated, including the capacity of the individual's immune system to synthesize antibodies and the degree of protection desired. Precise amounts of active ingredient required to be administered depend on the judgment of the practitioner. However, suitable dosage ranges are of the order of several hundred micrograms active ingredient per vaccination. Suitable regimes for initial administration and booster shots are also variable, but are typified by an initial administration followed by subsequent inoculations or other administrations.

The manner of application may be varied widely. Any of the conventional methods for administration of a pharmaceutical composition are applicable. These are believed to include oral application on a solid physiologically acceptable base or in a physiologically acceptable dispersion, parenterally, by injection and the like. The dosage of the pharmaceutical composition will depend on the route of administration and will vary according to the size and health of the subject.

In some embodiments, pharmaceutical compositions are administered to a subject. Different aspects of the present invention involve administering an effective amount of a composition to a subject. In some embodiments of the present invention, immunogenic compositions may be administered to the patient to protect against infection by one or more microbial pathogens. Additionally, such compounds can be administered in combination with an antibiotic or other known anti-microbial therapy. Such compositions will generally be dissolved or dispersed in a pharmaceutically acceptable carrier or aqueous medium.

The compositions and related methods, particularly administration of a peptide fibril/antigen complex may also be used in combination with the administration of traditional therapies. These include, but are not limited to, the administration of antibiotics such as streptomycin, ciprofloxacin, doxycycline, gentamycin, chloramphenicol, trimethoprim, sulfamethoxazole, ampicillin, tetracycline or various combinations of antibiotics. In cancer immunotherapy, the second therapy may be any cancer treatment such as surgery, chemotherapy, gene therapy, or radiation.

In one aspect, it is contemplated that a peptide fibril/immunogen composition and/or therapy is used in conjunction with antibacterial treatment or anticancer therapy. Alternatively, the therapy may precede or follow the other agent treatment by intervals ranging from minutes to weeks. In embodiments where the other agents and/or a proteins is administered separately, one would generally ensure that a significant period of time did not expire between the time of each delivery, such that the agent and antigenic composition would still be able to exert an advantageously combined effect on the subject. In such instances, it is contemplated that one may administer both modalities within about 12-24 h of each other and, more preferably, within about 6-12 h of each other. In some situations, it may be desirable to extend the time period for administration significantly, however, where several days (2, 3, 4, 5, 6 or 7) to several weeks (1, 2, 3, 4, 5, 6, 7 or 8) lapse between the respective administrations.

Various combinations may be employed, for example antibiotic therapy or cancer therapy is "A" and the immunogenic composition is "B":

A/B/A B/A/B B/B/A A/A/B A/B/B B/A/A A/B/B/B
B/A/B/B
B/B/B/A B/B/A/B A/A/B/B A/B/A/B A/B/B/A
B/B/A/A
B/A/B/A B/A/A/B A/A/A/B B/A/A/A A/B/A/A
A/A/B/A

Administration of the immunogenic compositions to a patient/subject will follow general protocols for the administration of such compounds, taking into account the toxicity, if any. It is expected that the treatment cycles would be repeated as necessary. It also is contemplated that various standard therapies, such as hydration, may be applied in combination with the described therapy.

The phrases "pharmaceutically acceptable" or "pharmacologically acceptable" refer to molecular entities and compositions that do not produce an adverse, allergic, or other untoward reaction when administered to an animal, or human. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in immunogenic and therapeutic compositions is contemplated. Supplementary active ingredients, such as other anti-cancer agents, can also be incorporated into the compositions.

The pharmaceutical compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Administration of the compositions will typically be via any common route. This includes, but is not limited to oral, nasal, or buccal administration. Alternatively, administration may be by orthotopic, intradermal, subcutaneous, intramuscular, intraperitoneal, intranasal, or intravenous injection. In certain embodiments, a vaccine composition may be inhaled (e.g., U.S. Pat. No. 6,651,655, which is specifically incorporated by reference). Such compositions would normally be administered as pharmaceutically acceptable compositions that include physiologically acceptable carriers, buffers or other excipients.

In addition to the compositions formulated for parenteral administration, such as those for intravenous or intramuscular injection, other pharmaceutically acceptable forms include, e.g., tablets or other solids for oral administration; time release capsules; and any other form currently used, including creams, lotions, mouthwashes, inhalants and the like.

The pharmaceutical compositions can be formulated for parenteral administration, e.g., formulated for injection via the intravenous, intramuscular, sub-cutaneous, or even intraperitoneal routes. Typically, such compositions can be prepared as injectables, either as liquid solutions or suspensions; solid forms suitable for use to prepare solutions or suspensions upon the addition of a liquid prior to injection can also be prepared; and, the preparations can also be emulsified.

Solutions of the pharmaceutical compositions as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

For parenteral administration in an aqueous solution, for example, the solution should be suitably buffered, if necessary, and the liquid diluent first rendered isotonic with sufficient saline or glucose. These particular aqueous solutions are especially suitable for intravenous, intramuscular, subcutaneous, and intraperitoneal administration. In this connection, sterile aqueous media which can be employed will be known to those of skill in the art in light of the present disclosure. For example, one dosage could be dissolved in isotonic NaCl solution and either added to hypodermoclysis fluid or injected at the proposed site of infusion, (see for example, Remington's Pharmaceutical Sciences, 1990). Some variation in dosage will necessarily occur depending on the condition of the subject. The person responsible for administration will, in any event, determine the appropriate dose for the individual subject.

An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the protection desired.

Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition.

VI. NANOFIBER APPLICATIONS

The nanofiber described herein may be used in many known applications employing nanofibers including, but not limited to, filter applications, computer hard drive applications, and pharmaceutical applications as described above. The nanofiber is useful in a variety of biological applications, including cell culture, tissue culture, and tissue engineering and cell delivery applications.

In one application, a nanofibrillar structure for cell culture and tissue engineering may be fabricated using the nanofiber. In an embodiment, the nanofibrillar structure comprises one or more nanofibers, wherein the nanofibrillar structure is defined by a network of one or more nanofibers comprising peptide A and peptide B. In another embodiment, the nanofibrillar structure comprises one or more nanofibers and a substrate wherein the nanofibrillar structure is defined by a network of one or more nanofibers deposited on a surface of the substrate. In another application, any cell culture including a growth media for cell culture may be prepared using the nanofiber.

In an embodiment, the growth media comprises a matrix of nanofibers in the form of a mat, roll, or sheet that may be adapted for insertion into a culture container. In another embodiment, the growth media comprises a matrix of nanofibers that is deposited onto a surface of a culture container or added as a fibrous mesh to the culture container. In another application, the nanofiber may be sprayed or spun onto a three-dimensional structure suitable for cell or tissue culture. The resultant three-dimensional structure is returned to a cell culture apparatus for continued growth where the electrospun fiber structure serves as a platform for growth of the cells.

In a further application, the nanofibers may be electrospun into nonwoven mesh and/or braids for the layered construction of three-dimensional matrices to serve as templates for tissue regeneration. In a further application, the nanofibers may be used as a cell culture medium in high throughput drug analysis and drug sensitivity analysis to increase the number of cells per well providing higher signal for detection of cell response. In another further application, the nanofibers may be used as a cell culture medium in high throughput drug analysis, drug sensitivity analysis, and other therapeutic schemes where the nanofibers provide an environment for the cells to more closely mimic the in vivo nature of the cells in an ex vivo environment.

The nanofibers may be formed as a cell culture or cell delivery matrix, for example, by including ECM proteins or ECM protein domains. In particular aspects, the cell culture or cell delivery matrix may comprise any degradable, bioabsorbable or non-degradable, biocompatible polymer. Exemplary three-dimensional culture or cell delivery materials include polymers and hydrogels comprising collagen, fibrin, chitosan, MATRIGEL™, polyethylene glycol, dextrans including chemically crosslinkable or photocrosslinkable dextrans, and the like. In an embodiment, the three-dimensional culture or cell delivery matrix comprises allogeneic components, autologous components, or both allogeneic components and autologous components. In an embodiment, the three-dimensional culture or cell delivery matrix comprises synthetic or semi-synthetic materials. In an embodiment, the three-dimensional culture or cell delivery matrix comprises a framework or support, such as a fibrin-derived scaffold. The term "scaffold" is used herein to include a wide variety of three-dimensional frameworks, for example, but not limited to a mesh, grid, sponge, foam, or the like.

VII. PROTEINACEOUS COMPOSITIONS

In certain embodiments, the present invention concerns novel compositions comprising at least one proteinaceous molecule and methods for preparing and using such compositions. The proteinaceous molecules may be used for forming a β-sheet structure or nanofiber or be packaged in the structure as an active compound attached to peptide A or non-β-sheet peptides.

As used herein, a "proteinaceous molecule," "proteinaceous composition," "proteinaceous compound," "proteinaceous chain" or "proteinaceous material" generally refers, but is not limited to, a protein of greater than about 200 amino acids or the full length endogenous sequence translated from a gene; a polypeptide of greater than about 100 amino acids; and/or a peptide of from about 3 to about 100 amino acids. All the "proteinaceous" terms described above may be used interchangeably herein. For convenience, the terms "protein," "polypeptide" and "peptide" may be used interchangeably herein.

In certain embodiments the size of the at least one proteinaceous molecule may comprise, but is not limited to, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or greater amino molecule residues, and any range derivable therein.

In some aspects the size of a peptide defined in certain aspects of the present invention may comprise, but is not limited to, 5, 6, 7, 8, 9, 10, 11, 12, 13, 14, 15, 16, 17, 18, 19, 20 amino acid residues. In other aspects the size of a peptide may comprise, but is not limited to, 5, 6, 7, 8, 9, 10, 11, 12, 13, 14, 15, 16, 17, 18, 19, 20, 21, 22, 23, 24, 25, 26, 27, 28, 29, 30 amino acid residues, or any range derivable therein. In certain embodiments, peptides less than or equal to 20 amino acids, or peptides 6-10 amino acids in length may be used.

As used herein, an "amino molecule" refers to any amino acid, amino acid derivative or amino acid mimic as would be known to one of ordinary skill in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

Accordingly, the term "proteinaceous composition" encompasses amino molecule sequences comprising at least one of the 20 common amino acids in naturally synthesized proteins, or at least one modified or unusual amino acid, including but not limited to those shown on Table 2 below.

TABLE 2

Modified and Unusual Amino Acids

| Abbr. | Amino Acid | Abbr. | Amino Acid |
|---|---|---|---|
| Aad | 2-Aminoadipic acid | EtAsn | N-Ethylasparagine |
| Baad | 3-Aminoadipic acid | Hyl | Hydroxylysine |
| Bala | β-alanine, β-Amino-propionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | AIle | allo-Isoleucine |
| Aib | 2-Aminoisobutyric acid | MeGly | N-Methylglycine, sarcosine |
| Baib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

In certain embodiments the proteinaceous composition comprises at least one protein, polypeptide or peptide. In further embodiments the proteinaceous composition comprises a biocompatible protein, polypeptide or peptide. As used herein, the term "biocompatible" refers to a substance which produces no significant untoward effects when applied to, or administered to, a given cell or organism according to the methods and amounts described herein. Organisms include, but are not limited to, Such untoward or undesirable effects are those such as significant toxicity or adverse immunological reactions. In particular embodiments, biocompatible protein, polypeptide or peptide containing compositions will generally be mammalian proteins or peptides or synthetic proteins or peptides each essentially free from toxins, pathogens and harmful immunogens.

Proteinaceous compositions may be made by any technique known to those of skill in the art, including the expression of proteins, polypeptides or peptides through standard molecular biological techniques, the isolation of proteinaceous compounds from natural sources, or the chemical synthesis of proteinaceous materials.

The nucleotide and protein, polypeptide and peptide sequences for various genes have been previously disclosed, and may be found at computerized databases known to those of ordinary skill in the art. One such database is the National Center for Biotechnology Information's Genbank and GenPept databases (available at www.ncbi.nlm.nih.gov/). The coding regions for these known genes may be amplified and/or expressed using the techniques disclosed herein or as would be known to those of ordinary skill in the art. Alternatively, various commercial preparations of proteins, polypeptides and peptides are known to those of skill in the art.

B. Purification or Isolation

In certain embodiments a protein or peptide or a composition comprising such a protein or peptide may be isolated or purified. Protein purification techniques are well known to those of skill in the art. These techniques involve, at one level, the homogenization and crude fractionation of the cells, tissue or organ to polypeptide and non-polypeptide fractions. The protein or polypeptide of interest may be further purified using chromatographic and electrophoretic techniques to achieve partial or complete purification (or purification to homogeneity). Analytical methods particularly suited to the preparation of a pure peptide are ion-exchange chromatography, gel exclusion chromatography, polyacrylamide gel electrophoresis, affinity chromatography, immunoaffinity chromatography and isoelectric focusing. An example of receptor protein purification by affinity chromatography is disclosed in U.S. Pat. No. 5,206,347, the entire text of which is incorporated herein by reference. A particularly efficient method of purifying peptides is fast performance liquid chromatography (FPLC) or even high performance liquid chromatography (HPLC).

A purified protein or peptide is intended to refer to a composition, isolatable from other components, wherein the protein or peptide is purified to any degree relative to its naturally-obtainable state. An isolated or purified protein or peptide, therefore, also refers to a protein or peptide free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95%, or more of the proteins in the composition.

A peptide, polypeptide or protein that is "purified to homogeneity," as applied to the present invention, means that the peptide, polypeptide or protein has a level of purity where the peptide, polypeptide or protein is substantially free from other proteins and biological components. For example, a purified peptide, polypeptide or protein will often be sufficiently free of other protein components so that degradative sequencing may be performed successfully.

Various methods for quantifying the degree of purification of the protein or peptide are known to those of skill in the art in light of the present disclosure. These include, for example, determining the specific activity of an active fraction, or assessing the amount of polypeptides within a fraction by SDS/PAGE analysis. A particular method for assessing the purity of a fraction is to calculate the specific activity of the fraction, to compare it to the specific activity of the initial extract, and to thus calculate the degree of purity therein, assessed by a "-fold purification number." The actual units used to represent the amount of activity will, of course, be dependent upon the particular assay technique chosen to follow the purification, and whether or not the expressed protein or peptide exhibits a detectable activity.

To purify a desired protein, polypeptide, or peptide a natural or recombinant composition comprising at least some specific proteins, polypeptides, or peptides may be subjected to fractionation to remove various other components from the composition. Various techniques suitable for use in protein purification are well known to those of skill in the art. These include, for example, precipitation with ammonium sulphate, PEG, antibodies and the like, or by heat denaturation, followed by: centrifugation; chromatography steps such as ion exchange, gel filtration, reverse phase, hydroxylapatite and affinity chromatography; isoelectric focusing; gel electrophoresis; and combinations of these and other techniques. As is generally known in the art, it is believed that the order of conducting the various purification steps may be changed, or that certain steps may be omitted, and still result in a suitable method for the preparation of a substantially purified protein or peptide.

Another example is the purification of a specific fusion protein using a specific binding partner. Such purification methods are routine in the art. Certain aspects of the present invention provide DNA sequences for the specific proteins, and any fusion protein purification method may be practiced. However, given many DNA and proteins are known, or may be identified and amplified using the methods described herein, any purification method can now be employed.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

Affinity chromatography is a chromatographic procedure that relies on the specific affinity between a substance to be isolated and a molecule to which it can specifically bind. This is a receptor-ligand type of interaction. The column material is synthesized by covalently coupling one of the binding partners to an insoluble matrix. The column material is then able to specifically adsorb the substance from the solution. Elution occurs by changing the conditions to those in which binding will not occur (e.g., altered pH, ionic strength, temperature, etc.). The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand.

C. Fusion Proteins

Other embodiments of protein conjugates concern fusion proteins. These molecules generally have all or a substantial portion of an antigenic peptide, linked at the N- or C-terminus, to all or a portion of a second polypeptide or protein. For example, fusions may employ leader sequences from other species to permit the recombinant expression of a protein in a heterologous host. Another useful fusion includes the addition of an immunologically active domain, such as an antibody epitope, to, for example, facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions.

In particular embodiments, the fusion proteins comprise a peptide tag attached to an antigenic protein or peptide. Examples of proteins or peptides that may be incorporated into a fusion protein include cytostatic proteins, cytocidal proteins, pro-apoptosis agents, anti-angiogenic agents, hormones, cytokines, growth factors, peptide drugs, antibodies, Fab fragments antibodies, antigens, receptor proteins, enzymes, lectins, MHC proteins, cell adhesion proteins and binding proteins. These examples are not meant to be limiting and it is contemplated that within the scope of the present invention virtually any protein or peptide could be incorporated into a fusion protein comprising a peptide tag. Methods of generating fusion proteins are well known to those of skill in the art. Such proteins can be produced, for example, by chemical attachment using bifunctional cross-linking reagents, by de novo synthesis of the complete fusion protein, or by attachment of a DNA sequence encoding a peptide tag to a DNA sequence encoding the second peptide or protein, followed by expression of the intact fusion protein.

D. Synthetic Peptides

Because of their relatively small size, the peptides in certain aspects can be synthesized in solution or on a solid support in accordance with conventional techniques. Various automatic synthesizers are commercially available and can be used in accordance with known protocols. See, for example, Stewart and Young, 1984; Tam et al., 1983; Merrifield, 1986; Barany and Merrifield, 1979, each incorporated herein by reference. Short peptide sequences, usually from about 6 up to about 35 to 50 amino acids, can be readily synthesized by such methods. Alternatively, recombinant DNA technology may be employed wherein a nucleotide sequence which encodes a peptide is inserted into an expression vector, transformed or transfected into an appropriate host cell, and cultivated under conditions suitable for expression.

E. Linkers/Coupling Agents

If desired, the compound or peptides of interest may be joined via a biologically-releasable bond, such as a selectively-cleavable linker or amino acid sequence. For example, peptide linkers that include a cleavage site for an enzyme preferentially located or active within a tumor environment are contemplated. Exemplary forms of such peptide linkers are those that are cleaved by urokinase, plasmin, thrombin, Factor IXa, Factor Xa, or a metallaproteinase, such as collagenase, gelatinase, or stromelysin.

Additionally, while numerous types of disulfide-bond containing linkers are known which can successfully be employed to conjugate moieties, certain linkers will generally be preferred over other linkers, based on differing pharmacologic characteristics and capabilities. For example, linkers that contain a disulfide bond that is sterically "hindered" are to be preferred, due to their greater stability in vivo, thus preventing release of the moiety prior to binding at the site of action.

Additionally, any other linking/coupling agents and/or mechanisms known to those of skill in the art can be used to combine to components or agents of the present, such as, for example, antibody-antigen interaction, avidin biotin linkages, amide linkages, ester linkages, thioester linkages, ether linkages, thioether linkages, phosphoester linkages, phosphoramide linkages, anhydride linkages, disulfide linkages, ionic and hydrophobic interactions, bispecific antibodies and antibody fragments, or combinations thereof.

Cross-linking reagents may be used to form molecular bridges that tie together functional groups of two different molecules, e.g., a stabilizing and coagulating agent. However, it is contemplated that dimers or multimers of the same analog can be made or that heteromeric complexes comprised of different analogs can be created. To link two different compounds in a step-wise manner, hetero-bifunctional cross-linkers can be used that eliminate unwanted homopolymer formation.

VIII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Figure 1:
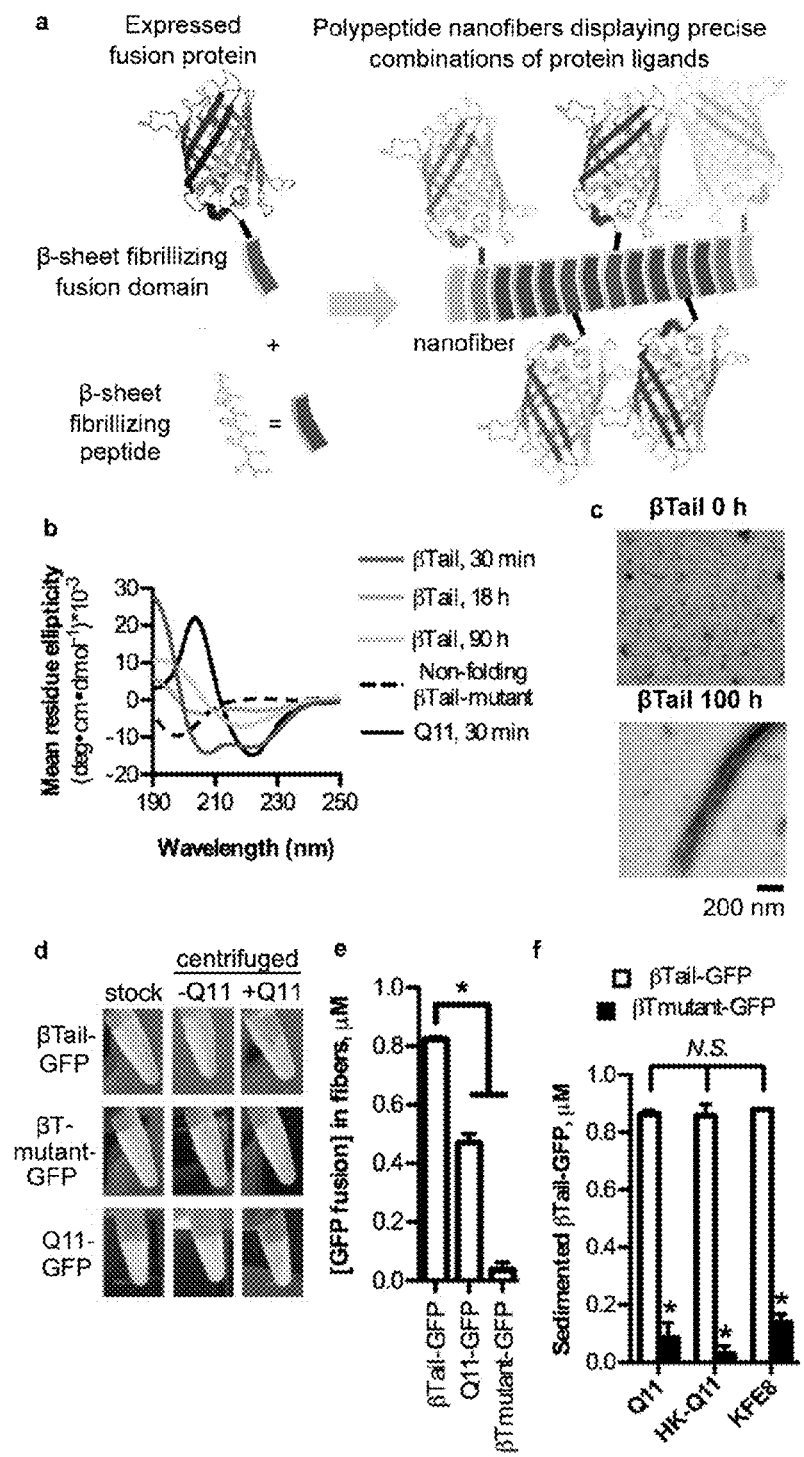
Figure 2:
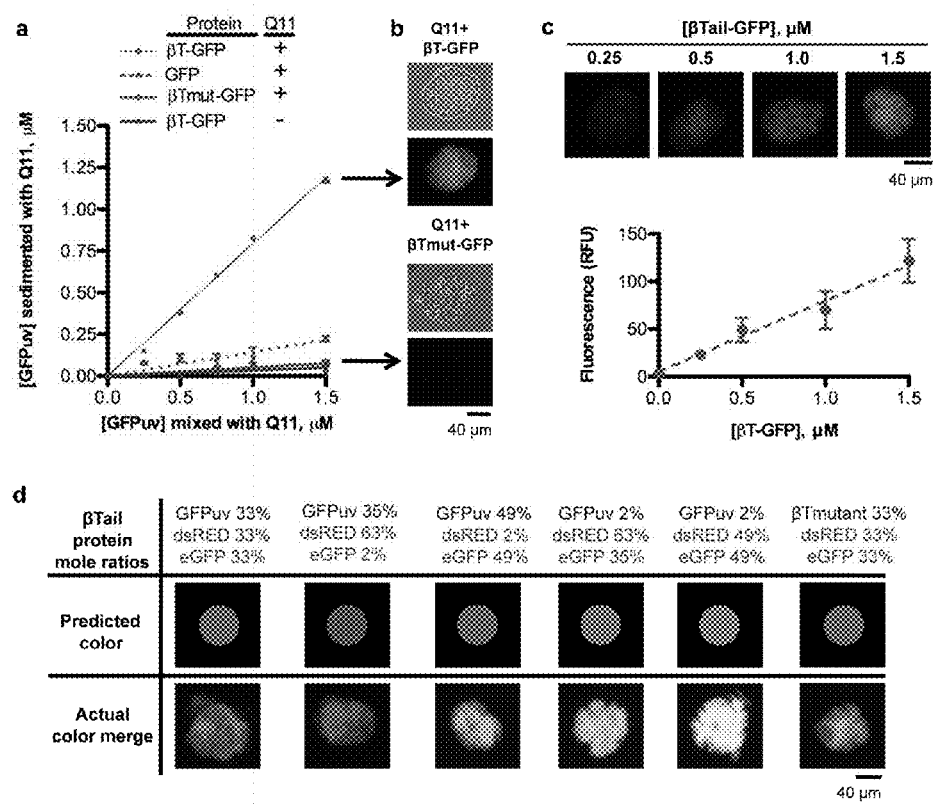
FIG. 2 (A-D): Fluorescent βTail fusion proteins integrated into Q11 nanofibers at a predictable dose without loss of activity.
Figure 6:
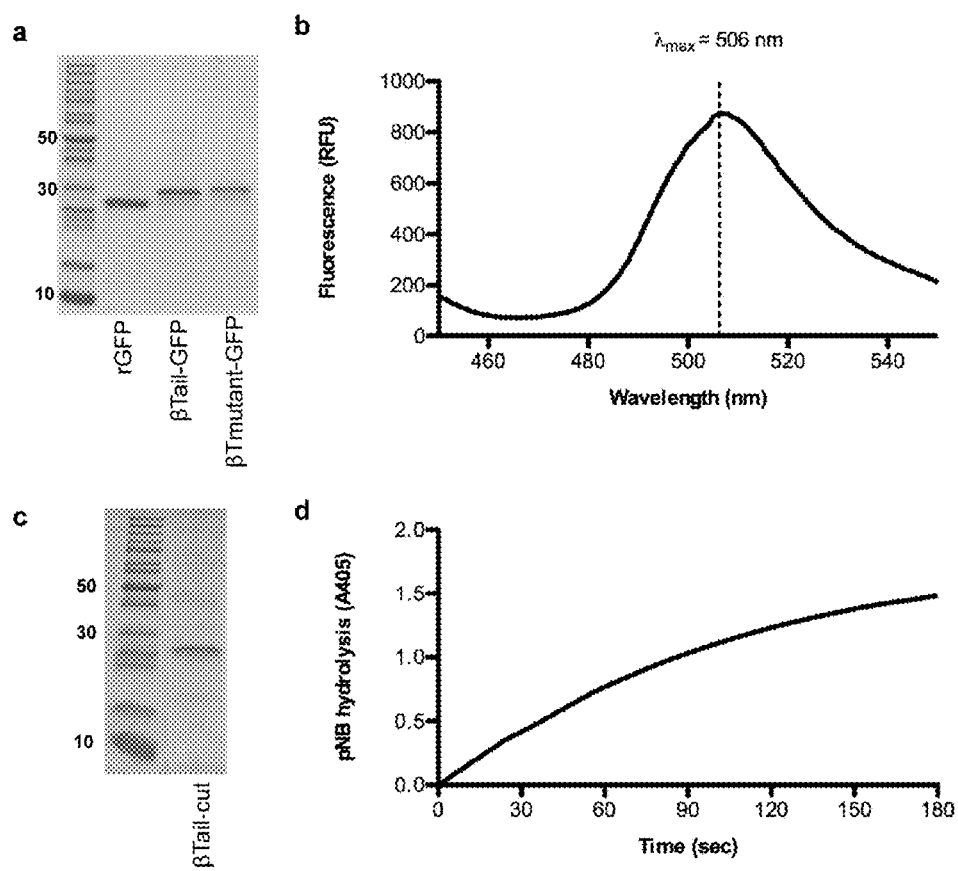
FIG. 6 (A-D): Active βTail-GFP (FIG. 6A-B) and βTail-cut (FIG. 6C-D) were recovered from the soluble phase following expression in E. coli, which demonstrated that the βTail domain did not induce aggregation or disrupt protein folding.
Figure 7:
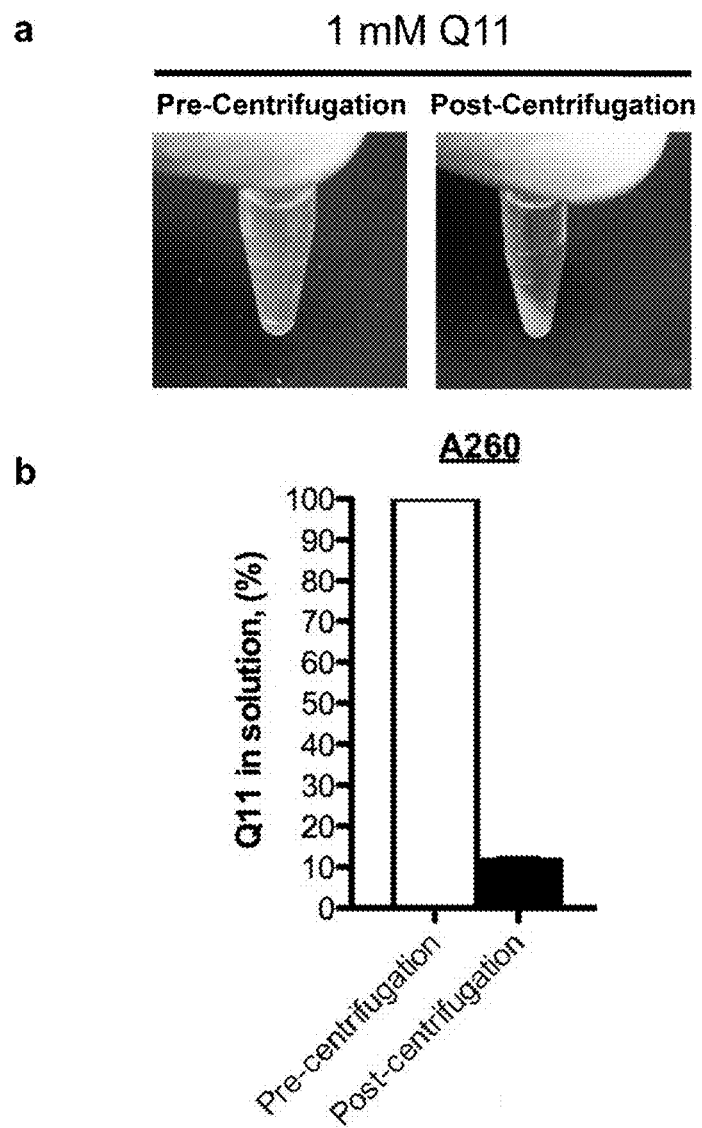
FIG. 7 (A-B): 1 mM Q11 nanofibers were efficiently sedimented by centrifugation at 12000×g for 5 min, as demonstrated by the formation of a pellet (FIG. 7A) and the loss of phenylalanine absorbance (λ=260 nm) in solution (FIG. 7B). N=3, mean±s.d.
Figure 8:
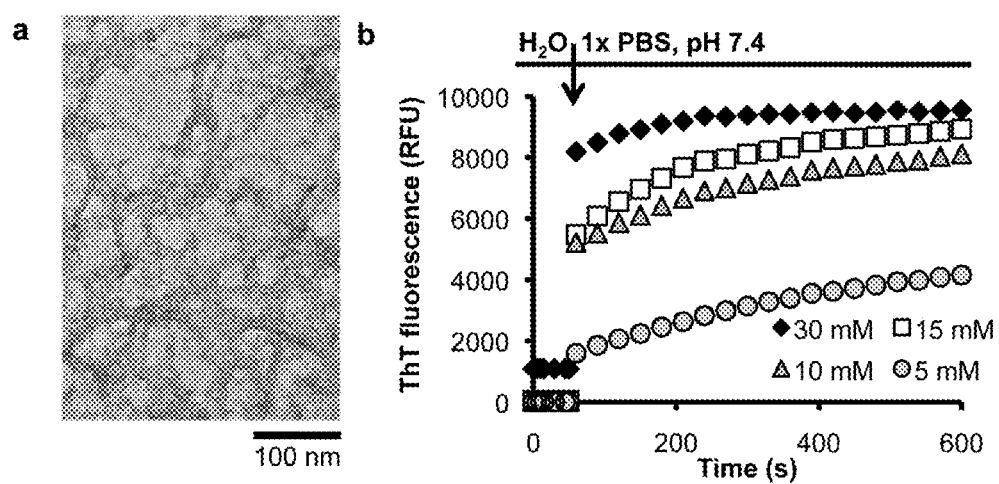
FIG. 8 (A-B): HK-Q11 self-assembled into β-sheet nanofibers in 1×PBS.

Supramolecular Assemblies with Precise Composition of Multiple Different Bioactive Protein Ligands An engineered variant of GFP having a β-sheet fibrillizing tail (i.e. a "βTail") integrated into nanofibers of β-sheet fibrillizing polypeptides in a βTail-dependent manner without loss of activity (FIG. 1). The βTail sequence, LKVELE-KLKSELVVLHSELHKLKSEL [SEQ ID NO. 3], was chosen because it underwent slow transition to a β-sheet (FIG. 1B-C) (Pagel, 2008). This property enabled the expression and subsequent assembly of βTail fusion proteins into nanofibers, as demonstrated by the recovery of active fluorescent and enzymatic βTail fusion proteins from the soluble phase following expression in E. coli (FIG. 6). This was in stark contrast to the rapid misfolding and aggregation of GFP fused to a β-sheet fibrillizing amyloid-β domain previously reported (Kim 2006), or the behavior of Q11-tagged fusion proteins, which could be expressed, but which did not assemble into nanofibers efficiently (FIG. 1D-E). Q11 peptide nanofibers were efficiently sedimented by centrifugation (FIG. 7), and >80% of βTail-GFP in solution sedimented with Q11 nanofibers (FIGS. 1D-E). On the other hand, GFP was primarily retained in the supernatant when the βTail domain was mutated to a non-folding variant, or when Q11 was used as the fusion tag (FIGS. 1D-E). In addition, βTail-GFP was retained in the supernatant when solutions lacked Q11 peptides (FIG. 1D), which demonstrated that βTail-GFP did not undergo significant self-assembly during the incubation period. βTail-GFP also efficiently integrated into nanofibers of HK-Q11 and KFE8, two other β-sheet fibrillizing polypeptides (FIG. 8) (Marini 2002), and this was again dependent on the βTail domain (FIG. 1E). On the other hand, both βTail-GFP and its mutated counterpart bound with similar efficiency to nanofibers of the β-sheet fibrillizing polypeptide RADA16 (data not shown) (Zhang 1995), which suggested that GFP interacted non-specifically with RADA16 nanofibers. Together, these observations indicated that βTail fusion proteins can integrate into β-sheet fibrillizing polypeptide nanofibers via the βTail domain, although the specificity of this interaction may be dependent on the primary sequence of the β-sheet fibrillizing polypeptide.

βTail-GFP integrated into Q11 nanofibers at a precise dose alone, or in combination with other fluorescent βTail fusion proteins, resulting in supramolecular biomaterials with precise composition of multiple different bioactive protein ligands (FIG. 2). βTail-GFP concentration in Q11 nanofibers sedimented by centrifugation correlated with βTail-GFP concentration in solution during nanofiber assembly (FIG. 2A). This was again dependent on the βTail domain and the presence of Q11, since GFP fused to a mutated βTail domain, as well as GFP lacking a fusion domain, were retained in the supernatant following centrifugation.

In addition, βTail-GFP was not sedimented by centrifugation in the absence of Q11 at any concentration tested, which demonstrated that βTail fusion proteins do not appreciably self-assemble over this concentration range (FIG. 2A). Q11 microgels were fluorescent when assembled in the presence of βTail-GFP, and this was also dependent on the βTail domain (FIG. 2B). βTail-GFP fluorescence was not perturbed when integrated into Q11 nanofibers, which was consistent with previous reports of GFP integrated into other polypeptide nanofibers (Baxa 2002), and GFP fluorescence could be dosed into Q11-based biomaterials by varying GFP concentration in solution during nanofiber assembly (FIG. 2C).

Similarly, fusions of βTail-GFPuv, βTail-enhanced GFP (βTail-eGFP), and βTail-dsRED monomer (βTail-dsRED) co-integrated into Q11 nanofibers at predictable concentrations, which correlated with the molar ratio of proteins present in solution during nanofiber assembly (FIG. 2D). In particular, a mixture consisting of an equimolar ratio of βTail-GFPuv, βTail-dsRED, and βTail-eGFP provided a gray Q11 microgel, which closely matched the predicted gray color for an RGB image with 33% red, 33% green, and 33% blue pixels. Varying the mole ratio of βTail-GFPuv, βTail-eGFP, and βTail-dsRED present during co-assembly enabled fine-tuning of Q11 microgel color, as demonstrated by microgels with colors ranging from pink to orange to teal that closely matched the predicted color (FIG. 2D). On the other hand, when a non-folding βTmutant-GFPuv variant was added in place of βTail-GFPuv in an equimolar mixture, the resulting microgels did not match the predicted gray color (FIG. 2D).

Together, these results demonstrated that multiple different βTail fusion proteins with a similar tertiary structure co-integrated into synthetic polypeptide nanofibers at a precise dose and in a βTail-dependent manner, without significantly perturbing protein bioactivity.

Figure 3:
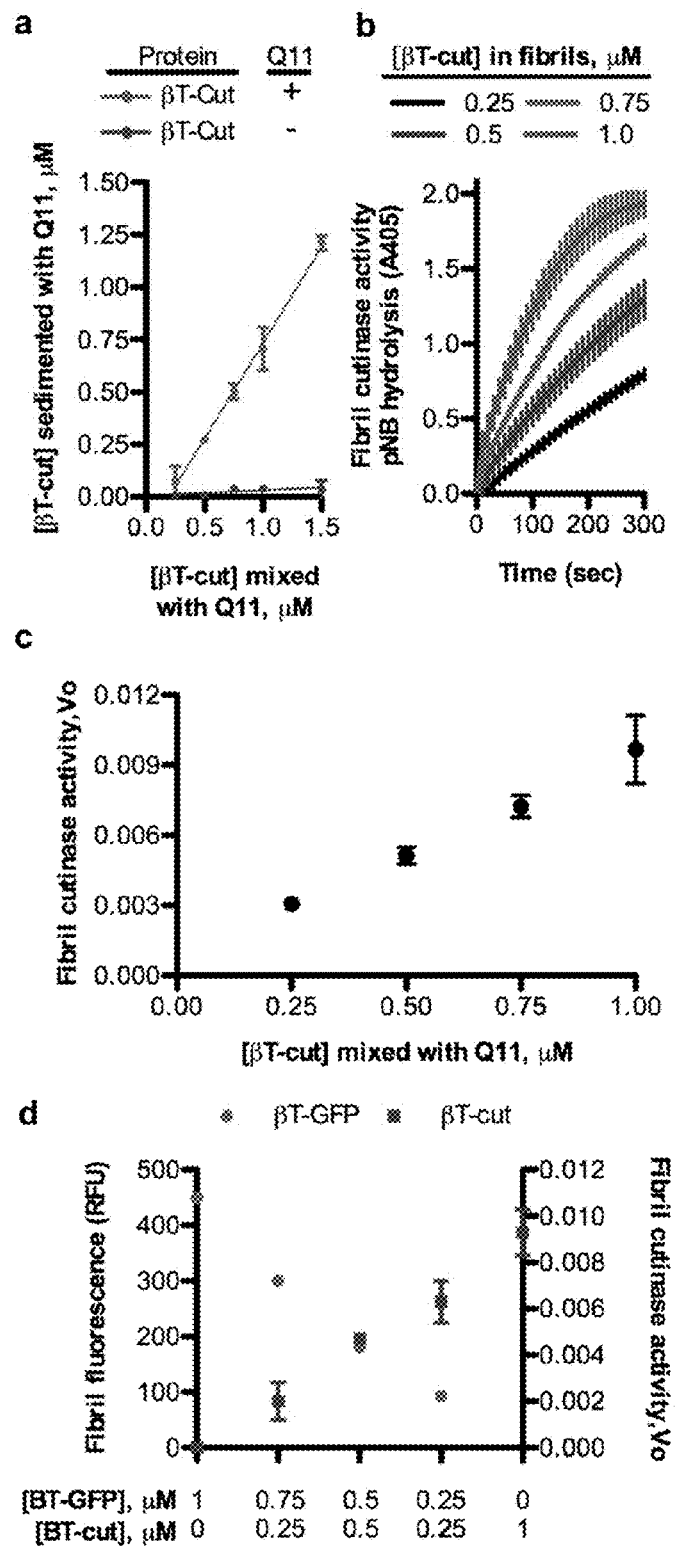
FIG. 3 (A-D): An enzymatic βTail fusion protein integrated into Q11 nanofibers at a predictable dose alone, or with varying amounts of βTail-GFP, without loss of activity.

Polypeptide nanofibers bearing a single protein antigen elicit robust, protein-reactive antibodies in the absence of additional immunostimulatory molecules (Hudalla 2013), and based on the data in this Example, this may be extended to include nanofibers bearing multiple different protein antigens would provide the basis for new subunit vaccines that approach the broad-spectrum, multi-antigen immunity conferred by live or attenuated pathogens It was demonstrated that a recombinant fusion of βTail and the fungal enzyme cutinase (βTail-cut) integrated into Q11 nanofibers without loss of activity to highlight the versatility of this approach (FIGS. 3A-3D), and because GFP and its homologs are relatively robust proteins that are broadly amenable to expression as recombinant fusions. βTail-cut concentration in Q11 nanofibers sedimented by centrifugation correlated with βTail-cut concentration in solution during Q11 assembly, and this was dependent on the presence of Q11 (FIG. 3A). Q11 nanofibers demonstrated cutinase activity when assembled in the presence of βT-cut, as measured by hydrolysis of p-nitrophenyl butyrate to p-nitrophenol (FIG. 3B) (Kolattukudy 1981), and cutinase activity could be dosed into Q11 nanofibers by simply varying βTail-cut concentration in solution during Q11 assembly (FIG. 3C). Notably, βTail-cut and βTail-GFP co-integrated into Q11 nanofibers at a predictable dose, without loss of activity, by varying the molar ratio of the proteins present during Q11 assembly (FIG. 3D). Importantly, this demonstrated that two distinct proteins having vastly different amino acid composition, tertiary structure, and bioactivity can be co-integrated into polypeptide nanofibers via the βTail fusion approach, suggesting the widespread potential of this system for creating biomaterials with new functional properties.

Figure 4:
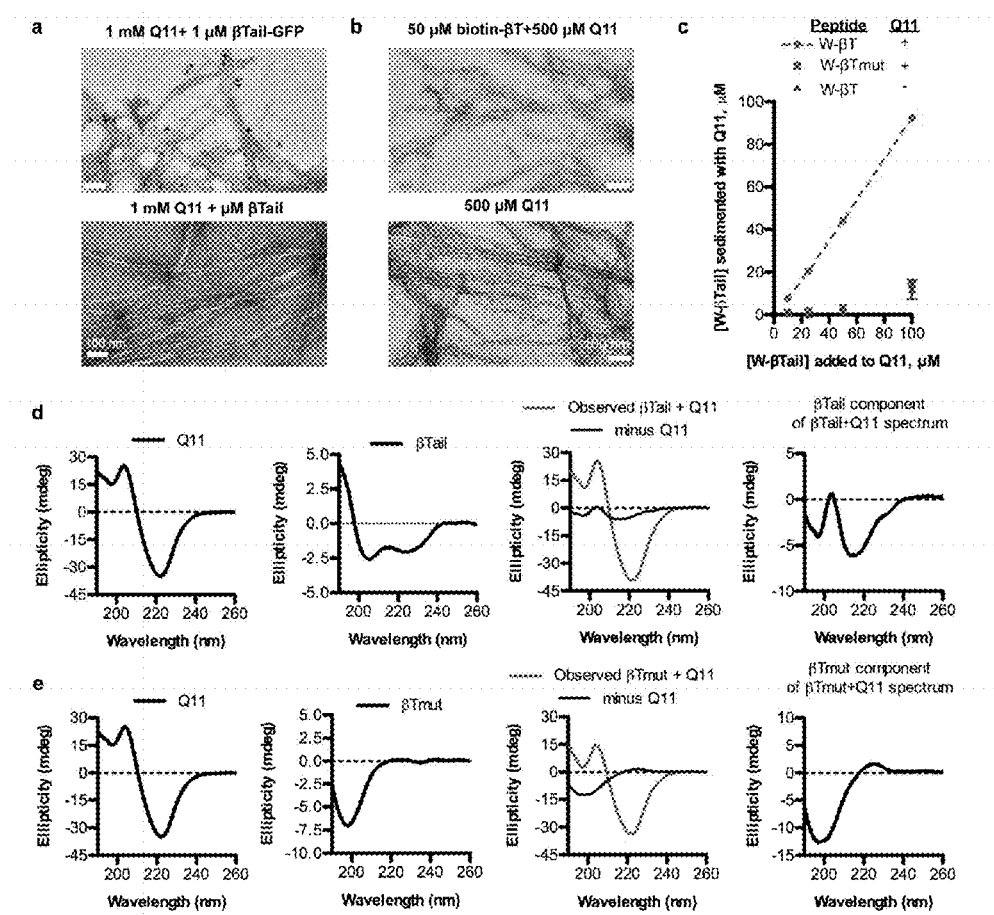
FIG. 4 (A-E): Q11 and βTail co-assembled into heterogeneous β-sheets.

Using TEM, the co-assembly of Q11 and βTail into heterogeneous β-sheet nanofibers was characterized in more detail (FIG. 4), based on the observations that Q11 and βTail self-assembled into β-sheet rich nanofibers independently (FIGS. 1B-C) (Pagel 2008; Collier 2003, each of which is incorporated herein for reference), and that βTail fusion proteins specifically interacted with Q11 nanofibers (FIG. 1-2). TEM identified a gold-labeled 2° antibody co-localized with Q11 nanofibers assembled in the presence of βT-GFPuv and then incubated with an anti-GFP antibody, whereas few gold-labeled 2° antibodies were associated with Q11 assembled in the presence of βT and then incubated with anti-GFP (FIG. 4A). These results further supported earlier observations that βT-GFP integrated into Q11 nanofibers (FIGS. 1D-E; FIG. 2A-B). TEM also identified gold-labeled streptavidin co-localized with Q11 nanofibers assembled in the presence of biotinylated-βTail, whereas gold-labeled streptavidin failed to bind to Q11 nanofibers assembled in the absence of biotinylated-βTail (FIG. 4B), demonstrating that βTail was integrated into Q11 nanofibers even in the absence of a large protein domain. Tryptophan-terminated βTail (W-βT) could be dosed into Q11 nanofibers at a precise concentration, as measured by loss of tryptophan fluorescence from the supernatant following centrifugation, and this was dependent on both the βTail sequence and the presence of Q11 (FIG. 4C). Taken together, these observations demonstrated that βTail polypeptides integrated into Q11 nanofibers in a sequence-specific manner, regardless of whether they were fused to a protein, a peptide, or a small molecule. This is noteworthy because it suggests that the βTail domain may be broadly useful for co-integrating various biologically active ligands into β-sheet nanofibers using the same simple mixing strategies commonly used to create multi-component nanofibers from different synthetic polypeptides having an identical self-assembling domain (Jung 2011; Gasiorowski, 2011).

Circular dichroism (CD) was used to further characterize Q11 and βTail co-assembly into heterogeneous β-sheets. βTail adopted an α-helical 2° structure in the absence of Q11, and transitioned to a predominantly β-sheet 2° structure in the presence of a 10-fold molar excess of Q11 (FIG. 4D). On the other hand, a non-folding, mutated βTail variant adopted a random coil conformation alone, as well as in the presence of excess Q11 (FIG. 4E). These observations were consistent with previous reports demonstrating significant changes to CD spectra following co-assembly of two different polypeptides into heterogeneous β-sheets (Takahashi 2002; Bothner 2003), and suggested that Q11 and βTail co-assembled into heterogeneous β-sheet nanofibers. Notably, the protein-bearing nanofibers described above (FIGS. 1-3) are likely also heterogeneous β-sheets, since they were prepared at a much greater Q11:βTail molar ratio (1000:1) than Q11:βTail solutions characterized by CD (10:1). Therefore, this approach provides a simple route to directly integrate one or more protein ligands at a precise concentration into β-sheet polypeptide nanofibers via non-covalent co-assembly, thereby eliminating the need rely on affinity tags or covalent capture ligands to immobilize protein ligands onto mature nanofibers at precise doses (Hudalla 2013; Sangiambut 2013).

Here, the ability of Q11 nanofibers bearing βTail-GFP to act as self-adjuvanting vaccines provided an initial demonstration of the biomedical potential of these materials (FIGS. 5A-5C). C57BL/6 mice immunized with βTail-GFP bearing nanofibers raised more circulating anti-GFP antibodies compared to mice immunized with soluble βTail-GFP (FIG. 5A). In addition, mice immunized with βTail-GFP bearing nanofibers underwent robust isotype switching towards predominantly IgG1 following primary and booster immunizations, whereas mice immunized with soluble βTail-GFP demonstrated a more balanced IgM/IgG1 isotype profile (FIG. 5B). C57BL/6 mice immunized with βTail-cut bearing nanofibers also raised more circulating anti-cut antibodies than mice immunized with soluble βTail-cut (FIG. 5C). These results demonstrated that polypeptide nanofibers bearing an integrated protein antigen act as vaccines to elicit adaptive immune responses against an antigen, and were consistent with a recent report demonstrating that Q11 nanofibers bearing covalently conjugated GFP elicited robust anti-GFP antibodies,[24] further suggesting the potential of these protein-bearing nanofibers for creating self-adjuvanting supramolecular vaccines. Because the βTail proteins were expressed in E. coli, significant steps were taken to ensure that the endotoxin content of all vaccines was ≤1 EU/mL, which is the maximum allowable dose for pre-clinical vaccines.[43] However, to further rule out the role of endotoxin in the observed immune responses, C57BL/6 mice lacking expression of Toll-like receptor-4 with Q11 nanofibers bearing βTail-GFP were immunized. These mice also raised high concentrations of circulating anti-GFP antibodies following immunization with βTail-GFP bearing nanofibers (FIG. 9), which demonstrated that endotoxin contaminants are not a key mediator of the observed responses. Together, these observations indicated that nanofibers bearing βTail fusion proteins acted as self-adjuvanting vaccines in the absence of additional immunostimulatory molecules, similar to nanofibers having a covalently conjugated protein,[24] suggesting that the nanofiber itself acts as the vaccine adjuvant to boost adaptive immune responses elicited against protein antigens.

Taken together, the results demonstrated that engineered fusion proteins having a β-sheet fibrillizing tail integrated into nanofibers of β-sheet fibrillizing polypeptides. Fluorescent and enzymatic proteins, for which bioactivity and tertiary structure are directly linked, were expressed as soluble, bioactive βTail fusion proteins and retained their native bioactivity when integrated into polypeptide nanofibers, which suggested the broad potential of this approach for integrating proteins with diverse biological or chemical activities into supramolecular assemblies. Varying the concentration of βTail fusion proteins present in solution during Q11 self-assembly provided precise control over protein content in the nanofibers, similar to approaches to immobilize folded proteins onto mature nanofibers via affinity tags or covalent capture ligands (Hudalla 2013; Sangiambut 2013). Notably, it was also demonstrated that multiple different βTail fusion proteins co-integrated into polypeptide nanofibers at a precise dose, resulting in supramolecular biomaterials displaying modular and tunable activity related to each protein. Although supramolecular assemblies with precise protein composition have been demonstrated previously (Brodin 2012; King 2012; Sinclair 2011), this could be the first demonstration of integrating multiple different protein ligands at precisely defined doses into supramolecular biomaterials. Importantly, this suggested the enormous potential of this general approach for creating novel biomaterials with unprecedented functional properties, which approach the biomolecular complexity inherent to supramolecular assemblies that govern diverse processes throughout living systems.

Here, it was observed that nanofibers with integrated βTail proteins elicited robust anti-protein antibodies in the absence of additional immunostimulatory molecules, suggesting the potential of these materials for developing new subunit vaccines for disease prophylaxis or immunotherapy. Creating efficacious multi-antigen vaccines is a key objective in modern vaccinology because of the potential for simultaneously raising broad-spectrum immunity against different pathogens or pathogen serotypes, while minimizing the number of immunization administered. An important consideration in the design of multi-antigen vaccines is the potential for "antigenic dominance", in which adaptive immune responses are selectively elicited against one antigen in a co-administered antigen mixture. The ability to precisely titrate two or more different antigens into polypeptide nanofiber adjuvants is likely to greatly improve efforts to minimize antigenic dominance during optimization of multi-antigen vaccine formulations, when compared to poorly controlled, non-specific antigen adsorption onto conventional adjuvants, such as aluminum hydroxide microparticles. However, in light of the general nature and unprecedented versatility afforded by this approach, it was contemplated that βTail fusion proteins, or analogous strategies, will be widely used to create supramolecular biomaterials for diverse medical and technological applications, including drug delivery, synthetic extracellular matrices for tissue engineering and 3-D culture, biosensors, and beyond.

Example 2

Materials and Methods

Peptide Synthesis.

Dimethylformamide, diethyl ether, trifluoroacetic acid (TFA), and dichloromethane were purchased from Fisher Scientific. Piperidine, p-nitrophenyl butyrate, and acetic acid were purchased from Sigma-Aldrich. All amino acids and Rink Amide AM resin were purchased from Novabiochem. The β-sheet fibrillizing polypeptides Q11 (QQKFQFQFEQQ) [SEQ ID NO. 6] (Kolattukudy 1981), HK-Q11 (QQKFQFQFHQQ) [SEQ ID. 7] (FIG. 8), KFE8 (FKFEFKFE) [SEQ ID NO. 8] (Marini 2002), and RADA16 (RADARADARADARADA) [SEQ ID NO. 20] (Zhang 1995), as well as βTail peptides, βTail (MALKVELEKLK-SELVVLHSELHKLKSEL [SEQ ID NO. 61]), W-βTail (WGSGSMALKVELEKLKSELVVLHSELHKLKSEL) [SEQ ID NO. 62], and βTail mutant (GKPEGEKPKSEGG-PGHSEGHKPKSEG) [SEQ ID NO. 63], were synthesized using a standard Fmoc solid-phase peptide synthesis protocol involving DIEA/HOBt/HBTU activation. Biotinylated-βTail was synthesized by reacting resin-bound $NH_2$—SGSG-βTail with Biotin-ONp (Novabiochem) at a 2.5:1 molar excess of biotin to primary amines in DMF overnight. Peptides were cleaved from the resin using 95% TFA/2.5% TIS/2.5% DI H2O and precipitated from the TFA cocktail using cold diethyl ether. Peptides were collected by centrifugation and washed five times in ether. The resulting peptide pellet was dried over vacuum, dissolved in deionized water, frozen, and lyophilized to dryness. Peptides were purified using a Varian ProStar HPLC system, Grace-Vydac C18 reverse-phase columns, and water-acetonitrile+0.1% TFA gradients to greater than 90% purity. Peptide molecular weight was verified using MALDI-TOF-MS on an Applied Biosystems Voyager system 6187 with α-cyano-4-hydroxycinnamic acid as the matrix.

Fusion Protein Construction.

The region encoding cutinase within a pET-21d vector containing the recombinant genetic fusion cutinase-(Gly-Ser linker)-GFPuv-His$_6$ (described previously in Hudalla 2013) was excised from the gene by digestion with NcoI and BamHI restriction enzymes. Complimentary oligonucleotides encoding βTail or βTmutant with an NcoI site at the 5' end and BamHI at the 3' end were synthesized by IDT DNA technologies (Iowa), annealed by heating to 95° C. for 3 min then allowing the heating block to cool to room temperature over 60 min, and digested with NcoI and BamHI restriction enzymes. Digested plasmid and oligonucleotides were purified by electrophoresis on a 1% agarose gel, followed by isolation with the QIAquick Gel Extraction kit (Qiagen). Oligonucleotides and plasmid were mixed at a 6:1 molar ratio in T4 DNA ligase buffer (New England Biolabs) heated at 45° C. for 1 min, spiked with 400 units of T4 DNA ligase, and incubated overnight at 18° C. Plasmids were then transformed into OneShot Top10 E. coli (Invitrogen) and grown on LB-agar plates with 100 ug/mL ampicillin. For expression, plasmids were isolated from Top10 E. coli using the QIAquick Miniprep kit (Qiagen), transformed into Origami B (DE3) E. coli, and grown on LB-agar plates with 100 ug/mL ampicillin and 50 ug/mL kanamycin. A pET-21d vector encoding βTail-cut was prepared using a similar method, except a nucleic acid sequence encoding cutinase was amplified out of the vector encoding cutinase-(Gly-Ser linker)-GFP using primers having a 5' BglII end and a 3' XhoI end. This gene and the pET-21d vector encoding βTail-(Gly-Ser linker)-GFP were digested with BglII and XhoI, purified, ligated together, and transformed into E. coli. Vectors encoding βTail-eGFP and βTail-dsRED were synthesized and subcloned into pET-21D by Genscript (New Jersey, USA). The sequence of each βTail fusion was confirmed by sequencing performed at the University of Chicago Sequencing Facility (see supplemental materials for fusion protein nucleotide and amino acid sequences).

Fusion Protein Expression and Purification.

Ten milliliters of 2×TY media with 100 μg/mL ampicillin and 50 μg/mL kanamycin A was inoculated with E. coli and maintained overnight at 37° C., 220 rpm. The 10 mL culture was subcultured into 1 L 2×TY with 100 μg/mL ampicillin and 50 μg/mL kanamycin A and maintained at 37° C., 220 rpm until an optical density of 0.6 at λ=600 nm was reached. Protein expression was then induced by adding 0.5 mM IPTG to the culture and maintaining the culture at 37° C., 100 rpm for 4 h. Cells were collected by centrifugation, washed, and lysed into 1×PBS containing 1× BugBuster Protein Extraction Reagent (Novagen, Calif.), 1 eComplete protease inhibitor tablet (Santa Cruz Biotechnology), 300 units DNAse I from bovine pancrease (Sigma-Aldrich, MO), and 100 μg lysozyme for 20 min at room temperature. The lysis buffer was cleared by centrifugation and His 6-tagged βTail fusion proteins were purified from the supernatant using metal-affinity chromatography on His Pur cobalt resin (Thermo Scientific, IL). Protein was eluted from the column with imidazole-containing buffers and concentrated into 1×PBS using centrifugal filter units with a 10,000 DA MWCO (Millipore). Endotoxin content was reduced using Triton X-114 cloud-point precipitation, according to previously reported methods (Hudalla 2013). Briefly, Triton X-114 was added to proteins at a 1:10 (v/v) ratio at 4° C., these solutions were maintained on ice for 20 min, and heated to 37° C. for 10 min. Endotoxin-loaded Triton X-114 micelles were then removed by centrifugation at 5000×g, and the process was repeated two additional times.

Nanofiber Assembly.

Lyophilized Q11 was dissolved in deionized water at a final concentration of 10 mM by vortexing for 5 min. Aqueous Q11 solutions were diluted 10-fold with 1×PBS containing GFP (Vector Labs cat# MB-0752), βTmutant-GFP, or one or more βTail fusion proteins at a total protein concentration between 0.25-1.5 μM, or tryptophan-terminated βTail (W-βTail) at a concentration between 10-100 μM. These solutions were then incubated under static conditions for nanofiber assembly, or on a LabNet Rocker 35 rocker table (speed setting 4) (New Jersey) to induce microgel formation.

Characterizing Protein Integration into Nanofibers.

Q11 nanofibers assembled overnight in the presence of βTail fusion proteins were sedimented by centrifugation at 12000×g for 5 min. The supernatant was removed and analyzed for βTail-GFP, βTmutant-GFP, GFP, or W-βTail content by measuring fluorescence emission with a SpectraMax M5 (excitation 395 nm/emission 503 nm for GFP; excitation 280 nm/emission 325 nm for W-βTail, glass-bottom 96-well plates were used for W-βTail fluorescence measurements), and converting emission intensity to protein concentration using GFP or W-βTail fluorescence standards. Additionally, nanofibers were resuspended in fresh 1×PBS, and nanofiber fluorescence was determined using a SpectraMax M5 plate reader. The μBCA assay kit (Pierce) was used according to the manufacturer's instructions to determine βTail-cut concentration in the supernatant. Protein concentration in the nanofibers was reported as the difference between the protein concentration in solution during nanofiber assembly and the protein concentration in the supernatant after centrifugation.

Fluorescence Microscopy.

Figure 5:
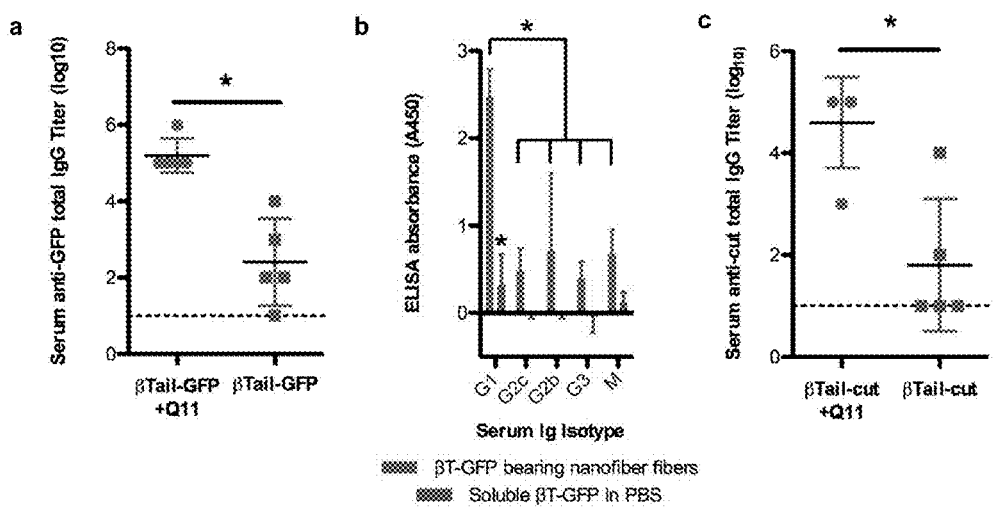
FIG. 5 (A-C): Q11 nanofibers bearing a βTail fusion protein acted as self-adjuvanting vaccines, eliciting robust antibodies against protein antigens in the absence of additional immunostimulatory factors.

Q11 microgel fluorescence was analyzed using a Zeiss Axioscope inverted epifluorescent microscope. Dapi filters were used to visualize βTail-GFPuv; FITC filters were used to visualize βTail-eGFP; and TRITC filters were used to visualize βTail-dsRED. Fluorescence emission of any protein with the inappropriate filter (e.g. βTail-GFPuv with FITC) was negligible (FIG. 5). Due to differences in the quantum efficiency of each protein, exposure time was adjusted until the grayscale image intensity of microgels containing 0.33 μM βTail-GFP, βTail-eGFP, or βTail-dsRED alone was similar (e.g. 0.75 sec for βTail-GFP, 1.5 sec for βTail-eGFP, and 2.5 sec for βTail-dsRED). These exposure times were then used to collect grayscale images of microgels formed from solutions containing βTail-GFP, βTail-eGFP, and βTail-dsRED at different molar ratios with each fluorophore filter cube. Grayscale microgel images were pseudocolored red, green, or blue according to the filter cube set used, and then merged using ImageJ software (NIH).

Cutinase Activity.

Cutinase hydrolyzes the colorless molecule p-nitrophenyl butyrate to the yellow molecule p-nitrophenol, which allows for colorimetric analysis of cutinase activity (Kolattukudy 1981). Cutinase activity of Q11 nanofibers assembled in the presence of 0.25-1.5 μM βTail-cut was analyzed by adding 1 μL of 0.1 M p-nitrophenyl butyrate (Sigma-Aldrich) in dimethyl sulfoxide (Fisher Scientific) to 100 μL of nanofibers in 1×PBS and measuring p-nitrophenol absorbance at 405 nm for 3 min using a SpectraMax M5 plate reader. The initial velocity, $v_o$, of p-nitrophenyl butyrate hydrolysis to p-nitrophenol was calculated from the linear portion of a plot of A405 nm versus time.

Transmission Electron Microscopy.

TEM was performed to visualize βTail-GFP or biotinylated-βTail integration into Q11 nanofibers using previously reported methods (Gasiorowski 2011), with minimal modifications. 1 mM Q11 was assembled in the presence of 1 μM βTail or 1 μM βTail-GFP, or 500 μM Q11 was assembled alone, or in the presence of 50 μM biotinylated-βTail, using methods outlined above. Nanofiber solutions were diluted to 0.25 mM Q11 with 1×PBS, and nanofibers were adsorbed onto 200 mesh lacey carbon grids, blocked with 2% acetylated bovine serum albumin (BSA)/0.1% cold water fish skin gelatin, and placed onto a series of droplets containing (1) monoclonal mouse anti-GFP antibody (Santa Cruz Biotechnology cat. #sc-9996, 1:4 in PBS), (2) goat anti-mouse IgG-15 nm gold particles (EMS cat. #25133), and streptavidin-5 nm gold particles (Invitrogen cat. # A32360, all particles diluted 1:4 in PBS), and (3) 1% uranyl acetate in water. Triplicate PBS washes were performed between staining steps. Grids were analyzed with an FEI Tecnai F30 TEM.

Circular Dichroism.

Circular dichroism was performed using an Aviv303 circular dichroism spectrometer in the University of Chicago Biophysics Core. Solutions containing 25 μM βTail or βTmutant, 250 μM Q11, 25 μM βTail plus 250 μM Q11, or 25 μM βTmutant plus 250 μM Q11 in 1× phosphate buffer plus 120 mM potassium fluoride were analyzed after overnight assembly under static conditions at room temperature. Each sample was analyzed 3 times, and the averaged spectrum was reported.

Immunizations.

Q11 microgels bearing βTail-GFP or βTail-cut were prepared as described above, except the materials were incubated at 4 deg C., rather than room temperature. GFP content in the microgels was analyzed fluorimetrically as described above, and the concentration of GFP in the microgels was used as the basis for βTail-GFP dose in the PBS group. Similarly, cutinase content in the microgels was analyzed with the μABCA assay kit (Pierce), according to the manufacturer's instructions, and βTail-cut dose in the microgels was used as the basis for βTail-cut dose in PBS group. Endotoxin content of all vaccines was analyzed with the Limulus Amoebocyte Lysate assay kit (Lonza) according to the manufacturer's instructions immediately before immunization, and all materials were below the upper limit of 1 EU/mL. Female C57BL/6 mice (6-8 weeks old, Taconic Farms, Ind.) were each given two 50 μL subcutaneous injections near the shoulder blades for each primary and booster immunization, similar to previously reported methods (Hudalla 2013). The GFP dosing regimen was: 90 nmol βTail-GFP with or without 1 mM Q11 at day 0, and 80 nmol βTail-GFP with or without 1 mM Q11 at day 31; the cutianse dosing regimen was: 108 nmol βTail-cut with or without 1 mM Q11 at days 0, 28, and 63. Blood was collected weekly via the submandibular vein. Institutional guidelines for the care and use of laboratory animals were strictly followed under a protocol approved by the University of Chicago's Institutional Animal Care and Use Committee.

ELISA.

ELISA was conducted as previously reported (Hudalla 2013), with minimal modifications. For mice immunized with βTail-GFP, serum collected at week 7 was analyzed; for mice immunized with βTail-GFP, serum collected at week 10 was analyzed. For all total IgG ELISAs, following overnight coating with 1 μg/mL βTmutant-GFP in PBS or PBS (negative control), all plates were washed 3 times with 0.5% Tween-20 in PBS. Wells were then blocked with 200 μL of 1% BSA/0.5% Tween-20 in PBS for 1 h at room temperature. This solution was removed from the wells, 100 μL of serum diluted $1:10^2$-$1:10^9$ in PBS with 1% BSA was then added directly to the wells without washing, and the plate was incubated for 1 h at room temperature. At the end of serum binding, the solution was removed from the plate, and the plates were washed 5 times with 0.5% Tween-20 in PBS. 100 μL of peroxidase-conjugated goat anti-mouse IgG (H+L) (Jackson Immuno Research, cat 115035003) diluted 1:5000 in PBS with 1% BSA was then added to the wells, and the plates were incubated for 45 min at room temperature. At the end of secondary antibody binding, the solution was removed and plates were washed 5 times with 0.5% Tween-20 in PBS. Plates were then developed by adding 100 μL of TMB substrate (eBioscience CA, cat 00-4201-56), incubating for 7.5 min at room temperature, then quenching the reaction with 50 μL of 1 M $H_3PO_4$. Absorbance was then measured at 450 nm with a SpectraMax M5 plate reader (Molecular Devices, CA).

For all isotyping ELISAs, following overnight coating with 1 μg/mL βTmutant-GFP in PBS or PBS, all plates were washed 3 times with 0.5% Tween-20 in PBS. Wells were then blocked with 200 μL of 1% BSA/0.5% Tween-20 in PBS for 1 h at room temperature. This solution was removed from the wells, 100 μL of serum collected at week 7 was diluted 1:500 in PBS with 1% BSA was then added directly to the wells without washing, and the plate was incubated for 1 h at room temperature. At the end of serum binding, the solution was removed from the plate, and the plates were washed 3 times with 0.5% Tween-20 in PBS. 100 μL of goat anti-mouse IgG1 (Sigma cat M5532), IgG2a/c (M5657), IgG2b (M5782), IgG3 (M5907), or IgM (M6157) diluted 1:1000 in PBS with 1% BSA was then added to the wells, and the plates were incubated for 30 min at room temperature. At the end of primary antibody binding, the solution was removed from the plate, and the plates were washed 3 times with 0.5% Tween-20 in PBS. 100 μL of peroxidase-conjugated rabbit anti-goat IgG diluted 1:5000 in PBS with 1% BSA was then added to the wells, and the plates were incubated for 15 min at room temperature. At the end of secondary antibody binding, the solution was removed from the plate, and the plates were washed 3 times with 0.5% Tween-20 in PBS. Plates were then developed by adding 100 μL of TMB substrate, incubating for 5 min at room temperature, then quenching the reaction with 50 μL of 1 M $H_3PO_4$. Absorbance was then measured at 450 nm with a SpectraMax M5 plate reader.

Example 3

βTail Fusion Proteins

All recombinant fusion protein genes were inserted between the NcoI and XhoI sites in pET-21d. Genetic and amino acid sequences for each βTail fusion protein are provided below.

| βTail-GFP | |
|---|---|
| Genetic Sequence: | ATGGCCCTGAAAGTGGAACTGGAAAAACTGAAAAGCGAACTGGTGGT<br>GCTGCATAGCGAACTGCATAAACTGAAAAGCGAACTGGGATCCGGCG<br>GTGGCGGTTCTGGTGGCGGTGGCTCTGGCGGTGGCGGCGGTGGAGGA<br>TCCGGCGGTGGCGGTTCTGGTGGCGGTGGCTCTGGCGGTGGCGGTTCT<br>AGTAAAGGAGAAGAACTTTTCACTGGAGTTGTCCCAATTCTTGTTGAA<br>TTAGATGGTGATGTTAATGGGCACAAATTTTCTGTCAGTGGAGAGGGT<br>GAAGGTGATGCAACATACGGAAAACTTACCCTTAAATTTATTTGCACT<br>ACTGGAAAACTACCTGTTCCATGGCCAACACTTGTCACTACTTTCTCTT<br>ATGGTGTTCAATGCTTTTCCCGTTATCCGGATCATATGAAACGGCATG<br>ACTTTTTCAAGAGTGCCATGCCCGAAGGTTATGTACAGGAACGCACTA<br>TATCTTTCAAAGATGACGGGAACTACAAGACGCGTGCTGAAGTCAAG<br>TTTGAAGGTGATACCCTTGTTAATCGTATCGAGTTAAAAGGTATTGAT<br>TTTAAAGAAGATGGAAACATTCTCGGACACAAACTCGAGTACAACTA<br>TAACTCACACAATGTATACATCACGGCAGACAAACAAAAGAATGGAA<br>TCAAAGCTAACTTCAAAATTCGCCACAACATTGAAGATGGATCCGTTC<br>AACTAGCAGACCATTATCAACAAAATACTCCAATTGGCGATGGCCCTG<br>TCCTTTTACCAGACAACCATTACCTGTCGACACAATCTGCCCTTTCGAA<br>AGATCCCAACGAAAAGCGTGACCACATGGTCCTTCTTGAGTTTGTAAC<br>TGCTGCTGGGATTACACATGGCATGGATGAGCTCTACAAACTCGAGCA<br>CCACCACCACCACCACTGA [SEQ ID NO. 64] |
| Amino Acid Sequence: | M A L K V E L E K L K S E L V V L H S E L H K L<br>K S E L G S G G G G S G G G G S G G G G G G G S<br>G G G G S G G G G S G G G G S S K G E E L F T G<br>V V P I L V E L D G D V N G H K F S V S G E G E<br>G D A T Y G K L T L K F I C T T G K L P V P W P<br>T L V T T F S Y G V Q C F S R Y P D H M K R H D<br>F F K S A M P E G Y V Q E R T I S F K D D G N Y<br>K T R A E V K F E G D T L V N R I E L K G I D F<br>K E D G N I L G H K L E Y N Y N S H N V Y I T A<br>D K Q K N G I K A N F K I R H N I E D G S V Q L<br>A D H Y Q Q N T P I G D G P V L L P D N H Y L S<br>T Q S A L S K D P N E K R D H M V L L E F V T A<br>A G I T H G M D E L Y K L E H H H H H H Stop<br>[SEQ ID NO. 65] |
| βTmutant-GFP | |
| Genetic Sequence: | ATGGCCGGAAAACCAGAAGGAGAAAAACCAAAATCAGAAGGAGGAC<br>CAGGACACTCAGAAGGACACAAACCAAAATCAGAAGGAGGATCCGG<br>CGGTGGCGGTTCTGGTGGCGGTGGCTCTGGCGGTGGCGGCGGTGGAG<br>GATCCGGCGGTGGCGGTTCTGGTGGCGGTGGCTCTGGCGGTGGCGGTT<br>CTAGTAAAGGAGAAGAACTTTTCACTGGAGTTGTCCCAATTCTTGTTG<br>AATTAGATGGTGATGTTAATGGGCACAAATTTTCTGTCAGTGGAGAGG<br>GTGAAGGTGATGCAACATACGGAAAACTTACCCTTAAATTTATTTGCA<br>CTACTGGAAAACTACCTGTTCCATGGCCAACACTTGTCACTACTTTCTC<br>TTATGGTGTTCAATGCTTTTCCCGTTATCCGGATCATATGAAACGGCAT<br>GACTTTTTCAAGAGTGCCATGCCCGAAGGTTATGTACAGGAACGCACT<br>ATATCTTTCAAAGATGACGGGAACTACAAGACGCGTGCTGAAGTCAA<br>GTTTGAAGGTGATACCCTTGTTAATCGTATCGAGTTAAAAGGTATTGA<br>TTTTAAAGAAGATGGAAACATTCTCGGACACAAACTCGAGTACAACT<br>ATAACTCACACAATGTATACATCACGGCAGACAAACAAAAGAATGGA<br>ATCAAAGCTAACTTCAAAATTCGCCACAACATTGAAGATGGATCCGTT<br>CAACTAGCAGACCATTATCAACAAAATACTCCAATTGGCGATGGCCCT<br>GTCCTTTTACCAGACAACCATTACCTGTCGACACAATCTGCCCTTTCGA<br>AAGATCCCAACGAAAAGCGTGACCACATGGTCCTTCTTGAGTTTGTAA<br>CTGCTGCTGGGATTACACATGGCATGGATGAGCTCTACAAACTCGAGC<br>ACCACCACCACCACCACTGA [SEQ ID NO. 66] |

```
Amino      M A G K P E G E K P K S E G G P G H S E G H K P
Acid       K S E G G S G G G G S G G G G S G G G G G G G S
Sequence:  G G G G S G G G G S G G G G S S K G E E L F T G
           V V P I L V E L D G D V N G H K F S V S G E G E
           G D A T Y G K L T L K F I C T T G K L P V P W P
           T L V T T F S Y G V Q C F S R Y P D H M K R H D
           F F K S A M P E G Y V Q E R T I S F K D D G N Y
           K T R A E V K F E G D T L V N R I E L K G I D F
           K E D G N I L G H K L E Y N Y N S H N V Y I T A
           D K Q K N G I K A N F K I R H N I E D G S V Q L
           A D H Y Q Q N T P I G D P V L L P D N H Y L S
           T Q S A L S K D P N E K R D H M V L L E F V T A
           A G I T H G M D E L Y K L E H H H H H H Stop
           [SEQ ID NO. 67]
```

βTail-dsRED

```
Genetic    ATGGCCGGAAAACCAGAAGGAGAAAAACCAAAATCAGAAGGAGGAC
Sequence:  CAGGACACTCAGAAGGACACAAACCAAAATCAGAAGGAGGATCCGG
           CGGTGGCGGTTCTGGTGGCGGTGGCTCTGGCGGTGGCGGCGGTGGAG
           GATCCGGCGGTGGCGGTTCTGGTGGCGGTGGCTCTGGCGGTGGCGGTT
           CTAGTGACGACAACACCGAGGACGTCATCAAGGAGTTCATGCAGTTC
           AAGGTGCGCATGGAGGGCTCCGTGAACGGCCACTACTTCGAGATCGA
           GGGCGAGGGCGAGGGCAAGCCCTACGAGGGCACCCAGACCGCCAAG
           CTGCAGGTGACCAAGGGCGGCCCCCTGCCCTTCGCCTGGGACATCCTG
           TCCCCCCAGTTCCAGTACGGCTCCAAGGCCTACGTGAAGCACCCCGCC
           GACATCCCCGACTACATGAAGCTGTCCTTCCCCGAGGGCTTCACCTGG
           GAGCGCTCCATGAACTTCGAGGACGGCGGCGTGGTGGAGGTGCAGCA
           GGACTCCTCCCTGCAGGACGGCACCTTCATCTACAAGGTGAAGTTCAA
           GGGCGTGAACTTCCCCGCCGACGGCCCCGTAATGCAGAAGAAGACTG
           CCGGCTGGGAGCCCTCCACCGAGAAGCTGTACCCCCAGGACGGCGTG
           CTGAAGGGCGAGATCTCCCACGCCCTGAAGCTGAAGGACGGCGGCCA
           CTACACCTGCGACTTCAAGACCGTGTACAAGGCCAAGAAGCCCGTGC
           AGCTGCCCGGCAACCACTACGTGGACTCCAAGCTGGACATCACCAAC
           CACAACGAGGACTACACCGTGGTGGAGCAGTACGAGCACGCCGAGGC
           CCGCCACTCCGGCTCCCAGCTCGAGCACCACCACCACCACCACTGA
           [SEQ ID NO. 68]
```

```
Amino      M A L K V E L E K L K S E L V V L H S H L E K L
Acid       K S E L G S G G G G S G G G G S G G G G G G G S
Sequence:  G G G G S G G G G S G G G G S S D D N T E D V I
           K E F M Q F K V R M E G S V N G H Y F E I E G E
           G E G K P Y E G T Q T A K L Q V T K G G P L P F
           A W D I L S P Q F Q Y G S K A Y V K H P A D I P
           D Y M K L S F P E G F T W E R S M N F E D G G V
           V E V Q Q D S S L Q D G T F I Y K V K F K G V N
           F P A D G P V M Q K K T A G W E P S T E K L Y P
           Q D G V L K G E I S H A L K L K D G G H Y T C D
           F K T V Y K A K K P V Q L P G N H Y V D S K L D
           I T N H N E D Y T V V E Q Y E H A E A R H S G S
           Q H H H H H H Stop [SEQ ID NO. 69]
```

βTail-eGFP

```
Genetic    ATGGCACTGAAAGTCGAACTGGAAAAACTGAAATCGGAACTGGTCGT
Sequence:  CCTGCACTCGCACCTGGAAAAACTGAAATCGGAACTGGGTAGCGGTG
           GCGGTGGCTCTGGTGGCGGTGGCAGTGGTGGCGGTGGCGGTGGCGGT
           TCCGGCGGTGGCGGTTCAGGCGGTGGCGGTTCGGGCGGTGGCGGTAG
           CTCTATGGTTAGCAAAGGTGAAGAACTGTTTACCGGCGTGGTTCCGAT
           TCTGGTCGAACTGGATGGTGACGTGAATGGCCATAAATTCAGTGTGTC
           CGGCGAAGGTGAAGGCGATGCGACCTATGGTAAACTGACGCTGAAAT
           TTATCTGCACCACGGGTAAACTGCCGGTTCCGTGGCCGACCCTGGTCA
           CCACGCTGACGTATGGTGTCCAGTGTTTCAGCCGCTACCCGGATCATA
           TGAAACAACACGACTTTTTCAAATCTGCGATGCCGGAAGGTTATGTGC
           AGGAACGTACCATTTTCTTTAAAGATGACGGCAACTACAAAACCCGCG
           CCGAAGTGAAATTTGAAGGTGATACGCTGGTTAACCGTATTGAACTGA
           AAGGCATCGATTTCAAAGAAGACGGTAATATCCTGGGCCATAAACTG
           GAATACAACTACAACTCACACAACGTCTACATTATGGCAGATAAACA
           GAAAAACGGTATCAAAGTGAACTTCAAAATCCGCCATAATATCGAAG
           ATGGCTCCGTTCAACTGGCTGACCACTATCAGCAAAACACCCCGATTG
           GTGATGGCCCGGTTCTGCTGCCGGACAATCATTACCTGTCAACGCAGT
           CGGCACTGAGCAAAGATCCGAACGAAAAACGTGACCACATGGTTCTG
           CTGGAATTTGTCACGGCTGCGGGTATTACGCTGGGTATGGACGAACTG
           TATAAACTCGAG [SEQ ID NO. 70]
```

```
Amino      M A L K V E L E K L K S E L V V L H S H L E K L
Acid       K S E L G S G G G G S G G G G S G G G G G G G S
Sequence:  G G G G S G G G G S G G G G S S M V S K G E E L
```

```
F T G V V P I L V E L D G D V N G H K F S V S G
E G E G D A T Y G K L T L K F I C T T G K L P V
P W P T L V T T L T Y G V Q C F S R Y P D H M K
Q H D F F K S A M P E G Y V Q E R T I F F K D D
G N Y K T R A E V K F E G D T L V N R I E L K G
I D F K E D G N I L G H K L E Y N Y N S H N V Y
I M A D K Q K N G I K V N F K I R H N I E D G S
V Q L A D H Y Q Q N T P I G D G P V L L P D N H
Y L S T Q S A L S K D P N E K R D H M V L L E F
V T A A G I T L G M D E L Y K H H H H H H Stop
[SEQ ID NO. 71]
```

βTail-cutinase

Genetic Sequence:
```
ATGGCCCTGAAAGTGGAACTGGAAAAACTGAAAAGCGAACTGGTGGT
GCTGCATAGCGAACTGCATAAACTGAAAAGCGAACTGGGATCCGGCG
GTGGCGGTTCTGGTGGCGGTGGCTCTGGCGGTGGCGGTTCTAGATCTG
GCCTGCCTACTTCTAACCCTGCCCAGGAGCTTGAGGCGCGCCAGCTTG
GTAGAACAACTCGCGACGATCTGATCAACGGCAATAGCGCTTCCTGCG
CCGATGTCATCTTCATTTATGCCCGAGGTTCAACAGAGACGGGCAACT
TGGGTACCCTCGGTCCTAGCATTGCCTCCAACCTTGAGTCCGCGTTCG
GCAAGGACGGTGTCTGGATTCAGGGCGTTGGCGGTGCCTACCGTGCCA
CTCTTGGAGACAATGCTCTCCCTCGCGGAACCTCTAGCGCCGCAATCA
GGGAGATGCTCGGTCTCTTCCAGCAGGCCAACACCAAGTGCCCTGACG
CGACTTTGATCGCCGGTGGCTACAGCCAGGGTGCTGCACTTGCAGCCG
CCTCCATCGAGGACCTCGACTCGGCCATTCGTGACAAGATCGCCGGAA
CTGTTCTGTTCGGCTATACCAAGAACCTACAGAACCGTGGCCGAATCC
CCAACTACCCTGCCGATAGGACCAAGGTCTTCTGCAATACAGGGGATC
TCGTTTGTACTGGTAGCTTGATCGTTGCTGCACCTCACTTGGCGTATGG
TCCTGATGCTCGTGGCCCTGCCCCTGAGTTCCTCATCGAGAAGGTTCG
GGCTGTCCGTGGTTCTGCTCTCGAGCACCACCACCACCACCACTGA
[SEQ ID NO. 72]
```

Amino Acid Sequence:
```
M A L K V E L E K L K S E L V V L H S E L H K L
K S E L G S G G G G S G G G G S G G G G S R S G
L P T S N P A Q E L E A R Q L G R T T R D D L I
N G N S A S C A D V I F I Y A R G S T E T G N L
G T L G P S I A S N L E S A F G K D G V W I Q G
V G G A Y R A T L G D N A L P R G T S S A A I R
E M L G L F Q Q A N T K C P D A T L I A G G Y S
Q G A A L A A A S I E D L D S A I R D K I A G T
V L F G Y T K N L Q N R G R I P N Y P A D R T K
V F C N T G D L V C T G S L I V A A P H L A Y G
P D A R G P A P E F L I E K V R A V R G S A L E
H H H H H H Stop [SEQ ID NO. 73]
```

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Baldwin, et al., *J Am Chem Soc.* 128:2162, 2006.
Baxa, et al., *PNAS USA.* 99:5253, 2002.
Black, et al., *Adv Mater.* 24:3845, 2012.
Bothner, et al., *J Am Chem Soc.* 125:3200, 2003.
Brodin, et al., *Nat. Chem.* 4:375, 2012.
Cardinale, et al., *Trends Biotechnol.* 30:369, 2012.
Collier & Messersmith, *Bioconjug Chem.* 14:748, 2003.
Collier & Segura, *Biomaterials.* 32:4198, 2011.
Collier, et al., *Chem Sox Rev.* 39:3413, 2010.
Collier, *Soft Matter.* 4:2310, 2008.
Gasiorowski & Collier, *Biomacromolecules.* 12:3549, 2011
Guglielmi, et al., *Biomaterials.* 30:829, 2009.
Guler, et al., *Bioconjug Chem.* 16:501, 2005.
Horii, et al., *PLoS One.* 2:e190, 2007.
Hudalla, et al., *Adv Healthc Mater.* Doi: 10.1002/adhm.201200435, 2013.
Jung, et al., *Integr Biol (Camb).* 3:185, 2011.
Kim, et al., *ACS Chem Biol.* 1:461, 2006.
King, et al., *Science.* 336:1171, 2012.
Kolattukudy, et al., *Meth Enzymol.* 71:652, 1981.
Leng, et al., *Angewandte Chemie Intl Ed.* 49:7243, 2010.
Lim, et al., *Chem Soc Rev.* 38:925, 2009.
Malyala & Singh, *J Pharm Sci.* 97:2041, 2008.
Marini, et al., *Nano Lett.* 2:295, 2002.
Matson & Stupp, *Chem Commun (Camb).* 48:26, 2012.
Matson, et al., *Chem Commun (Camb).* 47:7962, 2011.
Men, et al., *Nano Lett.* 9:2246, 2009.
Minten, et al., *Chem Sci.* 2:358, 2011.
Minten, et al., *J Am Chem Soc.* 131:17771, 2009.
Pagel, et al., *Chem Biochem.* 9:531, 2008.

Pagel, et al., *J. Am. Chem. Soc.* 128: 2196, 2006.
Patterson, et al., *ACS Nano.* 6:5000, 2012.
Rudra, et al., *PNAS USA.* 107:622, 2010.
Sangiambut, et al., *Adv Mater.* Doi: 10.1002/adma.201204127, 2013.
Sinclair, et al., *Nat Nanotechnol.* 6:558, 2011.
Sinthuvanich, et al., *J Am Chem Soc.* 134:6210, 2012.
Takahashi, et al., *Chem Biochem.* 3:637, 2002.
Veiga, et al., *Biomaterials.* 33:8907, 2012.
Wahome, et al., *Chem Biol Drug Des.* 80:349, 2012.
Wang, et al., *J Am Soc Nephrol.* 22:704, 2011.
Webber, et al., *Biomaterials.* 33:6823, 2012.
Wheeldon, et al., *J Mol Biol.* 392:129, 2009.
Wheeldon, et al., *PNAS USA.* 105:15275, 2008.
Woolfson & Mahmoud, *Chem Soc Rev.* 39:3464, 2010.
Zhang, et al., *Biomaterials.* 16:1385, 1995.

---

What is claimed is:

1. A nanofiber complex composition, wherein the composition comprises a β-sheet nanofiber structure comprising
a) a plurality of non-β-sheet peptide tags that undergo a transition from a non-β-sheet structure to a β-sheet structure in the presence of β-sheet peptides, wherein a non-β-sheet peptide tag is attached to a compound; and
b) a plurality of β-sheet peptides.

2. The composition of claim 1, wherein the structure comprises at least two different compounds.

3. The composition of claim 1, wherein the non-β-sheet peptides tags are α-helical peptides.

4. The composition of claim 1, wherein non-β-sheet peptides tags comprise one or more alpha helical motifs having a sequence of a b c de f g, with a and d being non-polar amino acids and e and g being charged amino acids.

5. The composition of claim 4, wherein a and/or d is Ala (A), Leu (L), Ile (I), Val (V) or a conservative derivative thereof in one or more of the alpha helical motifs.

6. The composition of claim 4, wherein a and/or d is Leu (L) in one or more of the alpha helical motifs.

7. The composition of claim 4, wherein e and/or g is Lys (K), Arg (R), His (H), Asp (D), Glu (E) or a conservative derivative thereof in one or more of the alpha helical motifs.

8. The composition of claim 4, wherein one or more of b, c, and f is a hydrophobic amino acid in one or more of the alpha helical motifs.

9. The composition of claim 4, wherein one or more of b, c, and f in one or more of the alpha helical motifs is Val (V), Tyr (Y), Phe (F), Trp (W), Ile (I), or Thr (T).

10. The composition of claim 4, wherein one or more of b, c, and f is Val (V) in one or more of alpha helical motifs.

11. The composition of claim 1, wherein the non-β-sheet peptide tag comprises an amino acid sequence having at least 90% identity with the sequence of LVVLHSELHKLKSEL (SEQ ID NO: 1), LVVLHSHLEKLKSEL (SEQ ID NO: 2), LKVELEKLKSELVVLHSELHKLKSEL (SEQ ID NO: 3), LKVELEKLKSELVVLHSHLEKLKSEL (SEQ ID NO: 4), or LKVELKELKKELVVLKSELKELKKEL (SEQ ID NO: 5).

12. The composition of claim 1, wherein one or more of the alpha helical motifs further comprise at least two metal binding amino acids spaced by one or three amino acids.

13. The composition of claim 1, wherein the non-β-sheet peptide tag has 14 to 56 amino acids in length.

14. The composition of claim 1, wherein the compound attached to the non-β-sheet peptide tags is a peptide, polypeptide, nucleic acid, small molecule, antigen, ligand, enzyme, reporter, drug, matrix, cell, virus, bacterium, lipid, carbohydrate, or a combination thereof.

15. The composition of claim 1, wherein at least one of the non-β-sheet peptide tags attached to a compound is a fusion protein.

16. The composition of claim 15, wherein one or more of the non-β-sheet peptide tags are attached to the amino-terminus of a peptide.

17. The composition of claim 1, wherein the compound attached to a non-β-sheet peptide tag is an enzyme, fluorescent protein, cell binding domain, cell adhesion domain, extracellular matrix domain, reporter protein, cytokine, antigen, signaling domain, immunomodulating protein, crosslinking protein, hormone, hapten, or a combination thereof.

18. The composition of claim 1, wherein the β-sheet peptides comprise a plurality of self-assembling peptides.

19. The composition of claim 1, wherein the β-sheet peptide has 2 to 40 amino acids in length.

20. A method of preparing a nanofiber complex composition of claim 1, comprising mixing the following:
a) a plurality of non-β-sheet peptide tags, wherein a non-β-sheet peptide tag is attached to a compound; and
b) a plurality of β-sheet peptides, under conditions that allow one or more of the non-β-sheet peptide tags to undergo transition from a non-β-sheet structure to a β-sheet structure, thereby preparing a nanofiber complex composition that forms a β-sheet structure comprising the transitioned non-β-sheet peptide tags and β-sheet peptides.

* * * * *